United States Patent
Otsuka et al.

(10) Patent No.: US 9,156,088 B2
(45) Date of Patent: Oct. 13, 2015

(54) AU—AG CORE-SHELL NANOROD PARTICLES AND METHOD FOR PRODUCING SAME

(75) Inventors: Hidenori Otsuka, Tokyo (JP); Toshihiko Kurosawa, Tokyo (JP); Yoshihiro Saito, Tokyo (JP); Koichi Kutsuzawa, Yokohama (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 764 days.

(21) Appl. No.: 13/514,838

(22) PCT Filed: Dec. 10, 2010

(86) PCT No.: PCT/JP2010/072288
§ 371 (c)(1),
(2), (4) Date: Jun. 8, 2012

(87) PCT Pub. No.: WO2011/071167
PCT Pub. Date: Jun. 16, 2011

(65) Prior Publication Data
US 2012/0244225 A1    Sep. 27, 2012

(30) Foreign Application Priority Data
Dec. 11, 2009   (JP) .................. 2009-282312

(51) Int. Cl.
| | | |
|---|---|---|
| A61K 9/14 | (2006.01) |
| B22F 1/00 | (2006.01) |
| B22F 1/02 | (2006.01) |
| B82Y 30/00 | (2011.01) |
| A61K 49/00 | (2006.01) |

(52) U.S. Cl.
CPC .............. B22F 1/0025 (2013.01); B22F 1/025 (2013.01); B82Y 30/00 (2013.01); A61K 49/0065 (2013.01)

(58) Field of Classification Search
CPC .................................................. A61K 49/0065
USPC .......................................................... 424/489
See application file for complete search history.

(56) References Cited

U.S. PATENT DOCUMENTS

2010/0046072 A1*   2/2010   Matsunami ................... 359/492

FOREIGN PATENT DOCUMENTS

| WO | 2009/084680 | 7/2009 |
| WO | 2009/096569 | 8/2009 |

OTHER PUBLICATIONS

Song et al, Crystal Overgrowth on Gold Nanorods: Tuning the Shape, Facet, Aspect Ratio, and Composition of the Nanorods, Chem. Eur. Eur. J, 2005, 11, 910-916.*
Wen, Synthesis of Nobel metal Nanoparticles Embedded in the Shell Layer of Core-Shell Poly(styrene-co-4-vinylpyridine) Microspheres and Their Application in Catalysis, Chem. Mater., 2008, 20, 2144-2150.*
J. Am. Chem. Soc., vol. 130, No. 32, pp. 10643-10647, 2008.
Chem. Lett., vol. 38, No. 1, pp. 60-61, 2009

* cited by examiner

*Primary Examiner* — Paul Dickinson
(74) *Attorney, Agent, or Firm* — Dilworth & Barrese, LLP

(57) ABSTRACT

Disclosed are: Au—Ag core-shell nanorod particles wherein a cationic surfactant such as CTAB is substituted by an other compound; and a method for producing the Au—Ag core-shell nanorod particles. Specifically disclosed are Au—Ag core-shell nanorod particles which are characterized in that each of the nanorod particles comprises a gold nanorod particle that serves as the core, a shell layer that covers the surface of the gold nanorod particle and is formed from silver, and a copolymer that adsorbs on the surface of the shell layer. The Au—Ag core-shell nanorod particles are also characterized in that the copolymer is a block copolymer or graft copolymer that is obtained by polymerizing at least a polymerizable monomer (A) that has a group represented by general formula (I). In the formula, $R^a$ represents an alkylene group having 2-7 carbon atoms.

20 Claims, 14 Drawing Sheets

FIG. 3
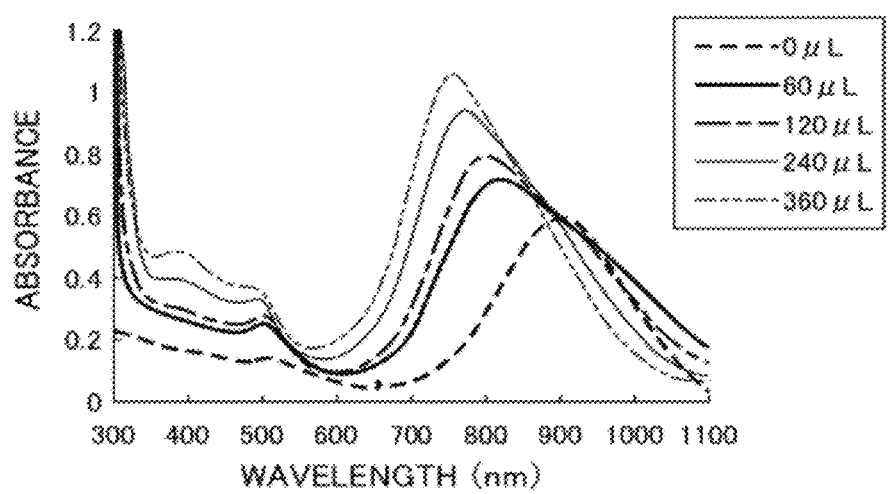
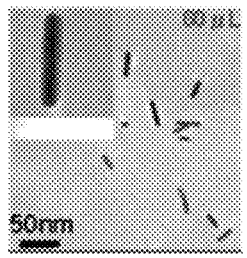
FIG. 4A
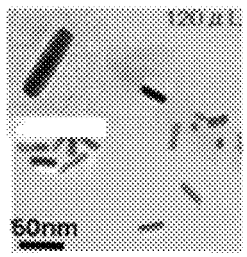
FIG. 4B
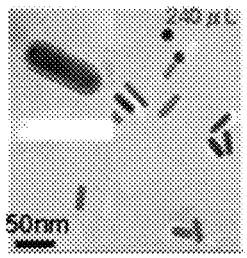
FIG. 4C
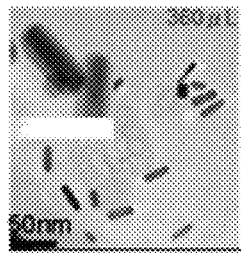
FIG. 4D

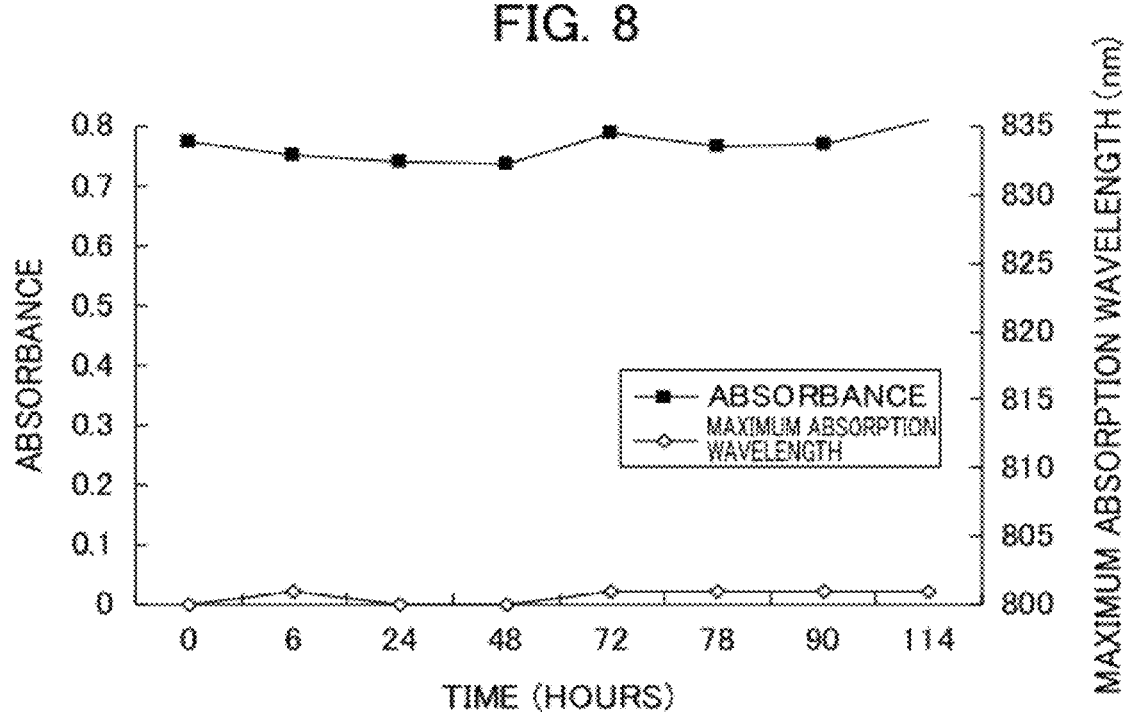

FIG. 16
| CONCENTRATION OF PARTICLES (μg/mL) | PHASE-CONTRAST MICROSCOPE | FLUORESCENCE MICROSCOPE |
|---|---|---|
| Control | 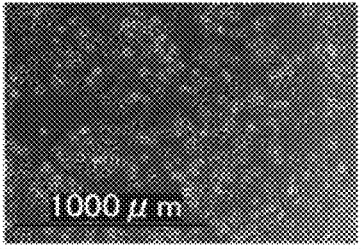 | 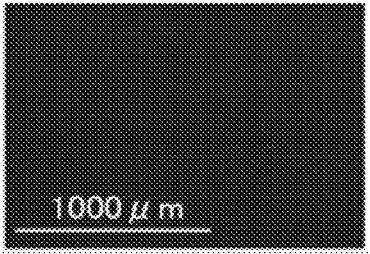 |
| 30 | 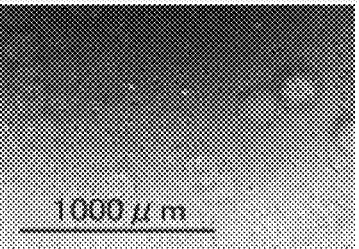 | 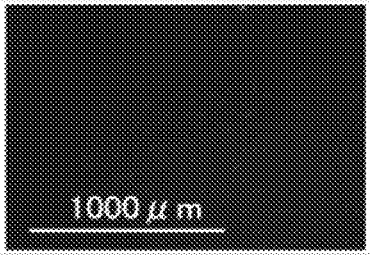 |
| 40 | 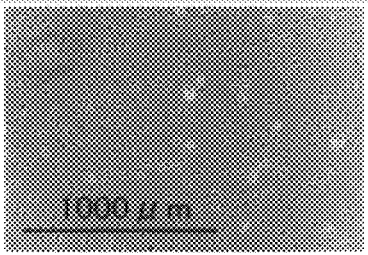 | 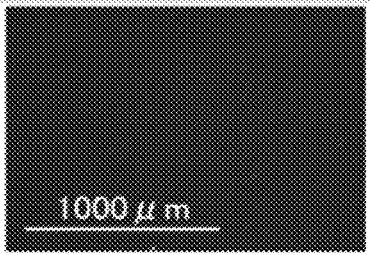 |
| 50 | 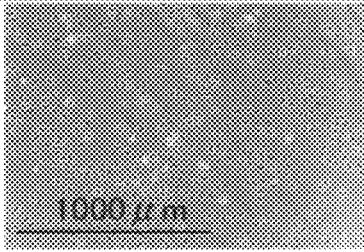 | 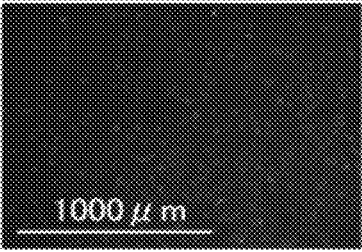 |
| 60 | 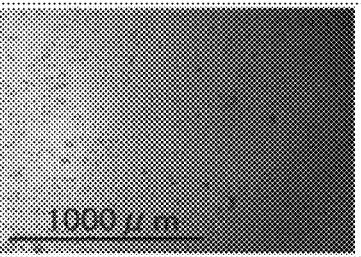 | 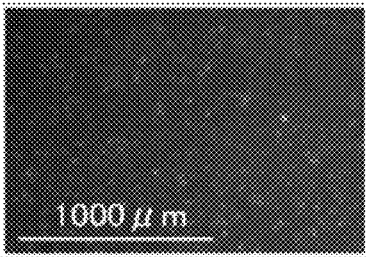 |

FIG. 17

AU—AG CORE-SHELL NANOROD PARTICLES AND METHOD FOR PRODUCING SAME

TECHNICAL FIELD

The present invention relates to Au—Ag core-shell nanorod particles and a method for producing the same.

BACKGROUND ART

Gold nanorod particles are nanoparticles of gold with a rod shape (bar-like shape) and show absorption at two wavelength ranges in a visible light range (ca. 520 nm) and a near-infrared range (ca. 900 nm). These are derived from surface plasmon resonance in short axis direction and long axis direction respectively, and the absorption at the near-infrared range is inherent to the gold nanorod particles. Furthermore, the absorbed optical energy is converted into heat, which is called as "photothermal effect". Since the transparency of biological material is higher in the near-infrared range, it is anticipated that the gold nanorod particles will find application in bio-imaging on the basis of intense near-infrared absorption capability thereof, photothermal treatment by use of heat generation, and the like, for example (see Non-Patent Documents 1, 2).

In recent years, Au—Ag core-shell nanorod particles are reported in which gold nanorod particles are cores and silver shell layers coat their surface (see Non-Patent Document 3). By way of coating with silver, absorption range of the particles shifts to blue. Furthermore, since silver-specific plasmon absorption is larger than that of gold, the photothermal effect can be enhanced by coating with silver.

Non-Patent Document 1: Drug Deliv. Syst., Vol. 24, No. 3, p. 260.

Non-Patent Document 2: J. Am. Chem. Soc., Vol. 130, No. 32, pp. 10643-10647.

Non-Patent Document 3: Chem. Lett., Vol. 38, No. 1, pp. 60-61.

DISCLOSURE OF THE INVENTION

Problems to be Solved by the Invention

Incidentally, gold nanorod particles are typically prepared within micelles of cationic surfactant such as CTAB (cetyltrimethylammonium bromide) and thus exist in a condition where their surface is protected by CTAB, etc. Au—Ag core-shell nanorod particles also exist in a condition where the surface of shell layers is protected by CTAB, etc. since they are prepared by depositing silver on the surface of gold nanorod particles protected by CTAB, etc. However, cationic surfactants such as CTAB exhibit very high cell cytotoxicity and thus are problematic in medical applications without countermeasure.

In regards to the gold nanorod particles, it has been reported that medical application thereof is possible by way of substituting a cationic surfactant such as CTAB into a compound (SH-PEG) of which a thiol group is bound to an end of polyethylene glycol chain (PEG chain) (see Non-Patent Documents 1, 2). However, substitution of a cationic surfactant such as CTAB into other compounds in this way has not been reported in regards to the Au—Ag core-shell nanorod particles. In accordance with the experiments of the present inventors, shell layer of silver cannot be formed when CTAB on the surface of the gold nanorod particles has been substituted into SH-PEG.

The present invention has been made in view of the problems described above; and it is an object of the present invention to provide Au—Ag core-shell nanorod particles of which the cationic surfactant such as CTAB is substituted into another compound and a method for producing the same.

Means for Solving the Problems

The present inventors have thoroughly investigated to attain the object described above and have found that the problems described above can be solved by substituting a cationic surfactant such as CTAB into a certain block copolymer or graft copolymer, thereby completing the present invention. Specifically, those explained below are provided.

In a first aspect, there are provided Au—Ag core-shell nanorod particles which are characterized in that each of the nanorod particles includes a gold nanorod particle that serves as a core, a shell layer that covers the surface of the gold nanorod particle and is formed from silver, and a copolymer that adsorbs on the surface of the shell layer, in which the copolymer is a block copolymer or graft copolymer that is obtained by polymerizing at least a polymerizable monomer (A) that has a group represented by general formula (I):

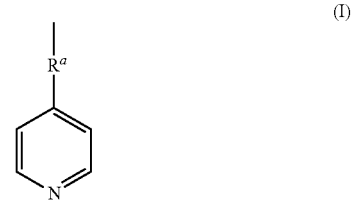

in which $R^a$ represents an alkylene group having 2-7 carbon atoms.

According to a second aspect of the present invention, in the Au—Ag core-shell nanorod particles according to the first aspect, the copolymer is a block copolymer or graft copolymer between the polymerizable monomer (A) and a polymerizable monomer (B) having a repeating structure represented by general formula (II):

in which $R^b$ represents an alkylene group having 2-5 carbon atoms and n represents any integer from 5 to 2,000.

According to a third aspect of the present invention, in the Au—Ag core-shell nanorod particles according to the first or second aspect, the polymerizable monomer (A) is represented by general formula (III):

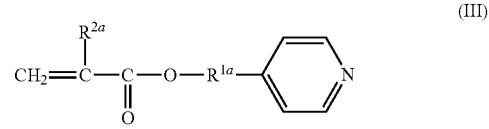

in which $R^{1a}$ represents an alkylene group having 2-7 carbon atoms and $R^{2a}$ represents a hydrogen atom or a methyl group.

According to a fourth aspect of the present invention, in the Au—Ag core-shell nanorod particles according to the second aspect, the polymerizable monomer (B) is represented by general formula (IV):

$$\begin{array}{c} R^{3b} \\ | \\ CH_2=C-C-O-(R^{2b}O)_n-R^{1b} \\ \| \\ O \end{array} \quad (IV)$$

in which $R^{1b}$ is a hydrogen atom or an alkyl group having 1-10 carbon atoms, $R^{2b}$ is an alkylene group having 2-5 carbon atoms, $R^{3b}$ is a hydrogen atom or a methyl group, and n represents any integer from 5 to 2,000.

According to a fifth aspect of the present invention, in the Au—Ag core-shell nanorod particles according to the second or fourth aspect, the polymerizable monomer (B) has a weight-average molecular weight from 200 to 80,000.

According to a sixth aspect of the present invention, in the Au—Ag core-shell nanorod particles according to the second, fourth, or fifth aspect, the mole ratio of the polymerizable monomer (A) to the polymerizable monomer (B) is from 1:99 to 99:1.

In a seventh aspect, there is provided a photothermal therapy drug which includes the Au—Ag core-shell nanorod particles according any one of the first to sixth aspects.

In a eighth aspect, there is provided a method for producing Au—Ag core-shell nanorod particles in which each of the nanorod particles includes a gold nanorod particle that serves as a core, a shell layer that covers the surface of the gold nanorod particle and is formed from silver, and a copolymer that adsorbs on the surface of the shell layer; the method including: a step of forming gold nanorod particles using a cationic surfactant as a mold, a step of forming gold nanorod particles on which a block copolymer or graft copolymer adsorbs by substituting the cationic surfactant into the block copolymer or graft copolymer, and a step of forming the shell layer by depositing silver on the surface of the gold nanorod particle on which the block copolymer or graft copolymer adsorbs, in which the copolymer is a block copolymer or graft copolymer that is obtained by polymerizing at least a polymerizable monomer (A) that has a group represented by general formula (I):

$$\begin{array}{c} | \\ R^a \\ \\ \text{[4-pyridyl group]} \end{array} \quad (I)$$

in which $R^a$ represents an alkylene group having 2-7 carbon atoms.

Effects of the Invention

In accordance with the present invention, there can be produced the Au—Ag core-shell nanorod particles in which the cationic surfactant such as CTAB is substituted into the block copolymer or graft copolymer obtained by polymerizing at least a polymerizable monomer (A) that has a group represented by general formula (I). Since the copolymer does not show toxicity to cells, medical treatment on the basis of the photothermal effect, which the Au—Ag core-shell nanorod particles provide, can be anticipated.

BRIEF DESCRIPTION OF THE DRAWINGS

FIG. 3 is a view that shows absorption spectra of dispersions of Py-g-PEG protected Au—Ag core-shell nanorod particles;

FIG. 4 is a view of Py-g-PEG protected Au—Ag core-shell nanorod particles observed by a transmission electron microscope (TEM) (additive amount of 1 mM $AgNO_3$ solution: (A) 60 μl, (B) 120 μl, (C) 240 μl, (D) 360 μl);

FIG. 8 is a view that shows dispersion stability of Py-g-PEG protected Au—Ag core-shell nanorod particles (within DMEM that contains 10% FBS);

FIG. 16 is a view that shows cell uptake by Py-g-PEG protected Au—Ag core-shell nanorod particles observed by a phase-contrast microscope and a fluorescence microscope; and FIG. 17 is a view that shows a photothermal effect on cells of Py-g-PEG protected Au—Ag core-shell nanorod particles observed by a phase-contrast microscope and a fluorescence microscope.

PREFERRED MODE FOR CARRYING OUT THE INVENTION

Figure 1:
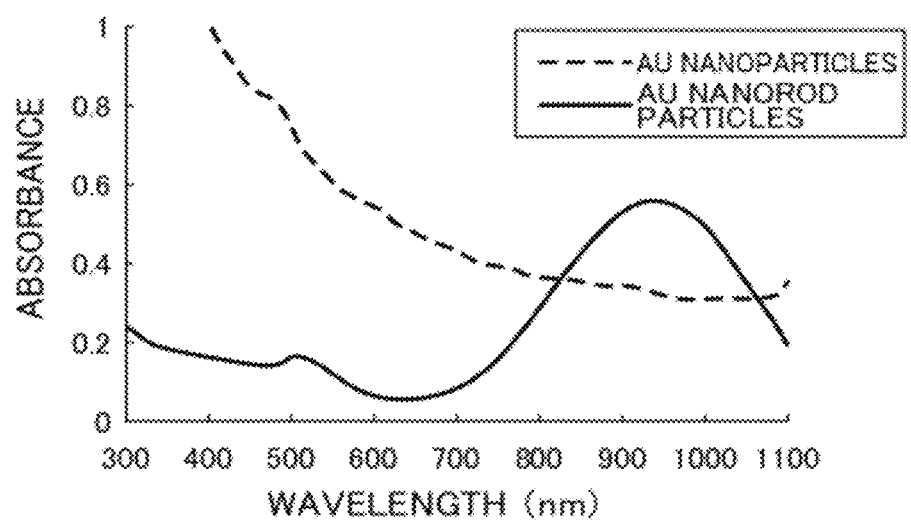
FIG. 1 is a view that shows absorption spectra of a dispersion of Py-g-PEG protected gold nanorod particles.

Hereinafter, the present invention is explained with respect to specific embodiments thereof; however, the present inven- Au—Ag Core-Shell Nanorod Particles In the Au—Ag core-shell nanorod particles of the present invention, each of the nanorod particles includes a gold nanorod particle that serves as the core, a shell layer that covers the surface of the gold nanorod particle and is formed from silver, and a copolymer that adsorbs on the surface of the shell layer. Here, the copolymer is a block copolymer or graft copolymer that is obtained by polymerizing at least a polymerizable monomer (A) that has a group represented by general formula (I).

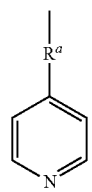
(I)

In the present invention, the gold nanorod particle refers to a nanoscale Au particle of which the ratio of a length in long axis direction to a length in short axis direction (aspect ratio) is greater than 1 and which has a rod (bar) shape. In regards to particle size of the gold nanorod particle, the length of long axis is preferably 10 to 500 nm and more preferably 20 to 200 nm. Furthermore, the length of short axis is preferably 1 to 500 nm and more preferably 1 to 50 nm. The particle size of the gold nanorod particle can be controlled by a concentration of gold ion in a preparation solution, for example. Lengths of long and short axes within the above-mentioned ranges leads to satisfactory dispersion stability. Besides, in regards to the gold nanorod particle of the present invention, the aspect ratio is preferably 1 to 10 and more preferably 1 to 5. An aspect ratio within the above-mentioned range leads to satisfactory dispersion stability. Additionally, the gold nanorod particle may be synthesized by a conventional process such as seed processes, alternatively commercially available ones may be employed.

In the Au—Ag core-shell nanorod particles of the present invention, the gold nanorod particle that serves as the core is covered by the shell layer that is formed from silver. The thickness of the shell layer to cover is not particularly limited as long as it uniformly covers the surface of the gold nanorod particle; typically, the thickness is 1 to 100 nm in long axis direction and 1 to 100 nm in short axis direction. Furthermore, the thickness is preferably 1 to 50 nm in long axis direction and 1 to 50 nm in short axis direction. The thickness of the shell layer can be controlled by the concentration of silver ions in the dispersion of gold nanorod particles, the aspect ratio of the gold nanorod particle, etc. The ranges described above may lead to excellent dispersion stability. Additionally, in the Au—Ag core-shell nanorod particles of the present invention, wavelength or intensity of the plasmon absorption can be controlled by changing the thickness of the shell layer, and the photothermal effect to convert absorbed light into thermal energy upon irradiation with near-infrared light can be enhanced by thickening the shell layer; therefore, the thickness may be appropriately set depending on the application considering the dispersion stability.

In the Au—Ag core-shell nanorod particles of the present invention, a copolymer adsorbs on the surface of the shell layer, in which the copolymer is a block copolymer or graft copolymer that is obtained by polymerizing at least a polymerizable monomer (A) that has a group represented by general formula (I).

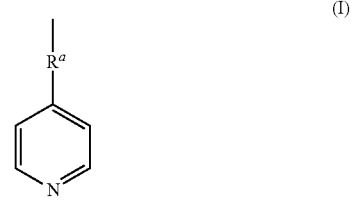
(I)

Polymerizable Monomer (A)

The polymerizable monomer (A) is a monomer that can polymerize and has a group represented by general formula (I). $R^a$ is characterized to be an alkylene group having 2-7 carbon atoms and preferably an alkylene group having 3-5 carbon atoms. In the present invention, the hydrophobic cohesion force between the Au—Ag core-shell nanorod particles can be controlled by changing the carbon number of the alkylene group of the copolymer. The Au—Ag core-shell nanorod particles with a small and stable particle size can be obtained by adjusting the carbon number of the alkylene group within this range.

The polymerizable monomer (A) is a monomer capable of polymerizing and thus requires a polymerizable group in its structure; and the species, which is not particularly limited, may be exemplified by a vinyl group, an allyl group, a styryl group, a methacryloyl group, an acryloyl group, etc. It can polymerize with the polymerizable monomer (B) described later via this polymerizable group.

It is preferred in the copolymer of the present invention that the polymerizable monomer (A) is represented by general formula (III).

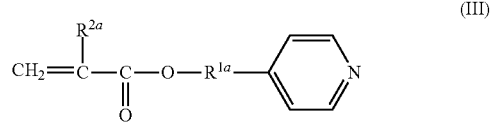
(III)

Here, $R^{1a}$ is an alkylene group having 2-7 carbon atoms, and preferably, is an alkylene group having 3-5 carbon atoms. Furthermore, $R^{2a}$ is a hydrogen atom or a methyl group.

Polymerizable Monomer (B)

The polymerizable monomer (B) is a monomer that can polymerize and has a repeating structure represented by general formula (II). $R^b$ is characterized to be an alkylene group having 2-5 carbon atoms and preferably 2-3 carbon atoms. Hydrophilicity and flexibility of the molecular may be enhanced by adjusting the carbon number of the alkylene group within this range. Furthermore, n is characterized to be any integer from 5 to 2,000 and preferably from 10 to 500. Hydrophilicity and flexibility thereof may be enhanced by adjusting n within this range. The unit of the repeating structure represented by general formula (II) is not particularly limited and is exemplified by ethylene oxide, propylene oxide, etc.

The polymerizable monomer (B) is a monomer capable of polymerizing and thus requires a polymerizable group in its structure; and the species of the functional group, which is not particularly limited, may be exemplified by a vinyl group, an allyl group, a styryl group, a methacryloyl group, an acryloyl group, etc. It can polymerize with the polymerizable monomer (A) described above via the polymerizable group.

It is preferred in the copolymer of the present invention that the polymerizable monomer (B) is represented by general formula (IV).

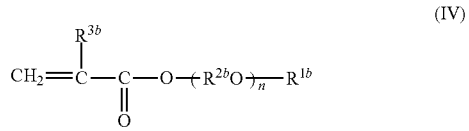

Here, $R^{1b}$ is a hydrogen atom or an alkyl group having 1-10 carbon atoms, and preferably, is an alkyl group having 2-5 carbon atoms. $R^{2b}$ is an alkylene group having 2-5 carbon atoms, and $R^{3b}$ is a hydrogen atom or a methyl group. Furthermore, n is characterized to be any integer from 5 to 2,000 and preferably from 10 to 500.

Polymerizable Monomer (C)

The polymerizable monomer (C) has a ligand.

The ligand may be exemplified by molecular recognition elements which exhibit a specific interaction with a certain objective substance including sugar chains, sugars, glycoproteins, glycolipids, antigens, antibodies, peptides, and nucleic acids such as oligo-DNAs and oligo-RNAs. Various functions can be added to the copolymer by bonding these ligands thereto.

The polymerizable monomer (C) is a monomer capable of polymerizing and thus requires a polymerizable group in its structure; and the species, which is not particularly limited, may be exemplified by a vinyl group, an allyl group, a styryl group, a methacryloyl group, an acryloyl group, etc. It can polymerize with the polymerizable monomer (A) described above via the polymerizable group.

It is preferred in the copolymer of the present invention that the polymerizable monomer (C) is represented by general formula (V).

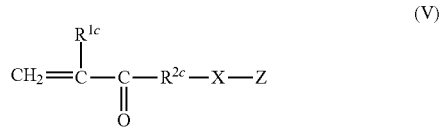

Here, $R^{1c}$ is a hydrogen atom or a methyl group, and $R^{2c}$ is —O— or —NH—. Furthermore, X is a spacer and Z is a ligand.

The spacer in the polymerizable monomer (C), which is not particularly limited as long as the ligands described above can be introduced, may be exemplified by oligoalkyleneoxy groups having a repeating unit number of 1 to 200, alkylene groups, etc.; and oligoethyleneoxy groups having a repeating unit number of 1 to 50 or alkylene groups are preferable. The alkylene groups may be linear or branched. The carbon number of the alkylene groups, which is not particularly limited, is preferably C1 to C8. Ethyleneoxy groups having a repeating unit number of 1 to 50 and alkylene groups of C1 to C8 are preferable since mobility of the copolymer becomes proper. Additionally, the ligand may be bound via the spacer in the copolymer.

Copolymer

The copolymer in the present invention is a block copolymer or graft copolymer that is obtained by polymerizing at least the polymerizable monomer (A). The polymerization process of the copolymer in the present invention, which is not particularly limited, may be a conventional process and is preferably a living radical polymerization process such as addition fragmentation chain transfer (RAFT) polymerization or atom transfer radical polymerization (ATRP). Molecular weight and distribution of the molecular weight of the copolymer to be synthesized can be controlled by the living radical polymerization process. Hereinafter, synthesis processes are exemplified with respect to the case where the copolymer in the present invention is a copolymer resulting from the copolymerization between the polymerizable monomer (A) and the polymerizable monomer (B). Here, the polymerization process is a living radical polymerization process.

Initially, the case of RAFT is exemplified. The polymerizable monomer (B), a chain transfer agent, and a polymerization initiator are dissolved in a predetermined solvent, and oxygen in a reaction container containing dissolved oxygen is completely removed, then they are heated to a temperature above the cleavage temperature of the polymerization initiator, and no higher than 100° C., for 24 to 48 hours, thereby synthesizing a macro chain transfer agent where the chain transfer agent has been introduced into an end of the polymer resulting from polymerization of the polymerizable monomer (B) (hereinafter, referred to as "B block"). Next, the macro chain transfer agent and the polymerizable monomer (A) are dissolved in a predetermined solvent, then heated to a temperature above the cleavage temperature of the polymerization initiator, and no higher than 100° C., for 24 to 300 hours, thereby the copolymer (block copolymer) of the present invention can be synthesized in which the B block and the polymer resulting from polymerization of the polymerizable monomer (A) (hereinafter, referred to as "A block") are bound linearly.

Furthermore, the polymerizable monomer (A), the polymerizable monomer (B), a chain transfer agent, and a polymerization initiator are dissolved in a predetermined solvent, then heated to a temperature above the cleavage temperature of the polymerization initiator, and no higher than 100° C., for 24 to 300 hours, thereby the copolymer (graft copolymer) of the present invention can be synthesized in which the B block and the A block are bound into a comb shape.

The polymerization initiator is not particularly limited and is exemplified by azo-type polymerization initiators such as 2,2'-azobisisobutyronitrile (AIBN) and 2,2'-azobis(2-methylbutyronitrile), sulfate salt polymerization initiators such as ammonium persulfate and potassium persulfate, and organic peroxide polymerization initiators such as benzoyl peroxide and lauroyl peroxide.

The amount of the polymerization initiator used is preferably 0.1% to 10% by mass based on the total amount of the polymerizable monomer (A) and the polymerizable monomer (B). A chain transfer agent such as mercaptoacetic acid, mercaptopropionic acid, 2-propanethiol, and 1-butanethiol may also be added in order to adjust the molecular weight in the case of graft copolymer.

Polymerization temperature and polymerization period are exemplified as described above, but they depend on temperature and property of intended final products. They are preferably 30° C. to 90° C. and more preferably 50° C. to 70° C. for 1 to 96 hours.

Next, the case of ATRP is explained. Initially, the polymerizable monomer (B), a halogenated alkyl agent, and a catalyst are dissolved in a predetermined solvent and allowed to react, thereby synthesizing a macro halogenated alkyl agent where the halogenated alkyl agent is introduced into an end of the B block. Next, the macro halogenated alkyl initiator and the polymerizable monomer (A) are dissolved in a predetermined solvent and a catalyst is further added thereto, then they are heated to a temperature above room temperature, and no higher than 100° C., for 6 to 50 hours, thereby the copolymer (block copolymer) of the present invention can be synthesized in which the B block and the A block are bound linearly.

The halogenated alkyl initiator used for ATRP is not particularly limited and is exemplified by 2-bromoisobutyryl bromide, 2-chloroisobutyryl bromide, bromoacetyl bromide, bromoacetyl chloride, and benzyl bromide.

Transition metal complexes of monovalent copper and divalent ruthenium may be used as the catalyst, for example.

Additionally, the solvent used for the polymerization reaction is not particularly limited and is exemplified by water, methanol, ethanol, propanol, t-butanol, benzene, toluene, N,N-dimethylformamide, tetrahydrofuran, chloroform, 1,4-dioxane, dimethyl sulfoxide, and mixed solutions thereof.

In the present invention, the weight-average molecular weight (measured by GPC using polystyrene as a standard substance) of the copolymer is preferably 1,000 to 500,000 and more preferably 2,000 to 100,000. Additionally, this range may impart the Au—Ag core-shell nanorod particles with interfacial stability.

In the present invention, the weight-average molecular weight (measured by GPC using polystyrene as a standard substance) of the polymerizable monomer (B) is preferably 200 to 80,000 and more preferably 500 to 20,000. Dispersion stability of the Au—Ag core-shell nanorod particles in the solvent can be controlled by changing the molecular weight of the polymerizable monomer (B). Additionally, this range may lead to stable dispersion of the Au—Ag core-shell nanorod particles in the solvent.

In the present invention, the mole ratio of (polymerizable monomer (A))/(polymerizable monomer (B)) is preferably 1:99 to 99:1 and more preferably 10:90 to 90:10. Hydrophile-lipophile balance can be controlled by changing the mole ratio of the polymerizable monomer (A) to the polymerizable monomer (B). Additionally, this range may lead to stable adsorption to the surface of the Au—Ag core-shell nanorod particles and also stable dispersion of the Au—Ag core-shell nanorod particles in the solvent.

In the Au—Ag core-shell nanorod particles of the present invention, the cationic surfactant such as CTAB with cell cytotoxicity is exchanged into the copolymer without cell cytotoxicity; therefore, medical applications such as medical inspection and therapy are possible. Furthermore, the Au—Ag core-shell nanorod particles of the present invention exhibit excellent dispersion stability in solutions containing salts and solutions containing sera. Accordingly, application for therapy of tumor tissues may be anticipated through the photothermal effect which the Au—Ag core-shell nanorod particles provide.

Photothermal Therapy Drug

The Au—Ag core-shell nanorod particles of the present invention can be used as a photothermal therapy drug. In addition to subcutaneous injection into an affected area to be treated and intravenous injection, surgical means may be exemplified as the administration route of the photothermal therapy drug that contains the Au—Ag core-shell nanorod particles of the present invention, for example. In the case of using the Au—Ag core-shell nanorod particles of the present invention as the photothermal therapy drug, the affected area is irradiated with light for a certain period after the Au—Ag core-shell nanorod particles of the present invention are administered. Wavelength range of the light is preferably 500 to 1,500 nm and more preferably 700 to 900 nm. This range of wavelength may lead to effective heat generation by the Au—Ag core-shell nanorod particles of the present invention. The means of light irradiation may be exemplified by light sources of laser, pulse laser. Furthermore, in the case of using the Au—Ag core-shell nanorod particles of the present invention as the photothermal therapy drug, the disease to be treated is exemplified by cancer.

Method for Producing Au—Ag Core-Shell Nanorod Particles

Hereinafter, the method for producing Au—Ag core-shell nanorod particles of the present invention is explained. Here, explanations common to those of Au—Ag core-shell nanorod particles described above are omitted.

The method for producing Au—Ag core-shell nanorod particles of the present invention is characterized in including: a step of forming gold nanorod particles using a cationic surfactant as a mold, a step of forming gold nanorod particles on which a block copolymer or graft copolymer adsorbs by substituting the cationic surfactant into the block copolymer or graft copolymer, and a step of forming a shell layer by depositing silver on the surface of the gold nanorod particle on which the block copolymer or graft copolymer adsorbs, in which the copolymer is a block copolymer or graft copolymer that is obtained by polymerizing at least a polymerizable monomer (A) that has a group represented by general formula (I).

Specifically, the Au—Ag core-shell nanorod particles of the present invention may be produced by the processes below. Initially, the gold nanorod particles are produced by a conventional process such as seed processes. Specifically, a reducing agent is added and stirred in a solution that contains a cationic surfactant and a gold acid halide to deposit gold, thereby preparing a dispersion of gold nanoparticles. Next, the gold acid halide is added to a solution that contains a cationic surfactant and an inorganic silver salt, then to which a reducing agent is further added and stirred. The dispersion of gold nanoparticles is added and stirred in the resulting solution, thereby preparing the dispersion of gold nanorod particles protected by the cationic surfactant. Here, commercially available ones may be used as the gold nanorod particles.

Here, quaternary ammonium salts such as hexadecyltrimethylammonium bromide (CTAB) and hexadecyltrimethylammonium chloride (CTAC) may be favorably used as the cationic surfactant, for example. Chloroauric acid may be favorably used as the gold acid halide, for example. Sodium borohydride may be favorably used as the reducing agent, for example.

Next, the dispersion of gold nanorod particles protected by the cationic surfactant is subjected to centrifugal separation, then the resulting precipitate is dispersed and stirred in the solution containing the copolymer, followed by dialysis using a dialysis membrane. The dialyzed dispersion is subjected to centrifugal separation, then the precipitate is dispersed into water, thereby preparing the dispersion of gold nanorod particles protected by the copolymer.

Here, the centrifugal separation is preferably carried out at 20,000 to 140,000 rpm. A regenerated cellulose membrane having a molecular weight cut off of 2,000 to 10,000 is preferably used as the dialysis membrane. Supernatant fluid containing the cationic surfactant with high toxicity is removed by the centrifugal separation and then dialysis is carried out using the dialysis membrane; thereafter the copolymer is adsorbed onto the surface of the gold nanorod particles.

Subsequently, an inorganic silver salt is added to the dispersion of gold nanorod particles protected by the copolymer, then a reducing agent and a base are added in series and stirred, followed by dialysis using a dialysis membrane. The dialyzed dispersion is subjected to centrifugal separation, then the precipitate is dispersed into water, thereby preparing the dispersion of Au—Ag core-shell nanorod particles protected by the copolymer.

Here, the inorganic silver salt is exemplified by silver nitrate and silver acetate, and silver nitrate is preferable in view of excellence in dispersion stability, toxicity, etc. The amount of the inorganic silver salt used is typically 0.1 to 5 equivalents to gold nanorod and preferably 0.1 to 1 equivalents thereto. This range may provide the Au—Ag core-shell nanorod particles with excellent dispersion stability. Additionally, the thickness of the shell layer can be controlled by adjusting the amount of the inorganic silver salt used.

Sodium borohydride, ascorbic acid, and citric acid may be exemplified as the reducing agent, and ascorbic acid is preferable in view of excellent controllability of reduction reaction. Sodium hydroxide and potassium hydroxide may be exemplified as the base, and sodium hydroxide is preferable in view of easy availability and lower price.

EXAMPLES

The present invention is explained more specifically with reference to examples below; however, the present invention is not limited to the descriptions.

Synthesis of Graft Copolymer

A polymerizable monomer (A) and a polymerizable monomer (B) were copolymerized to synthesize a graft copolymer (Py-g-PEG) as shown in the reaction scheme below.

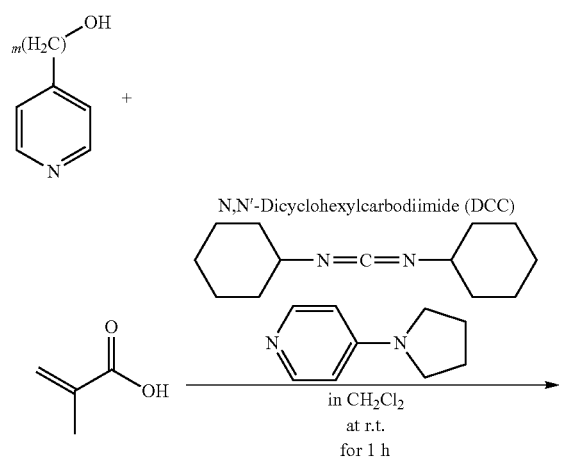

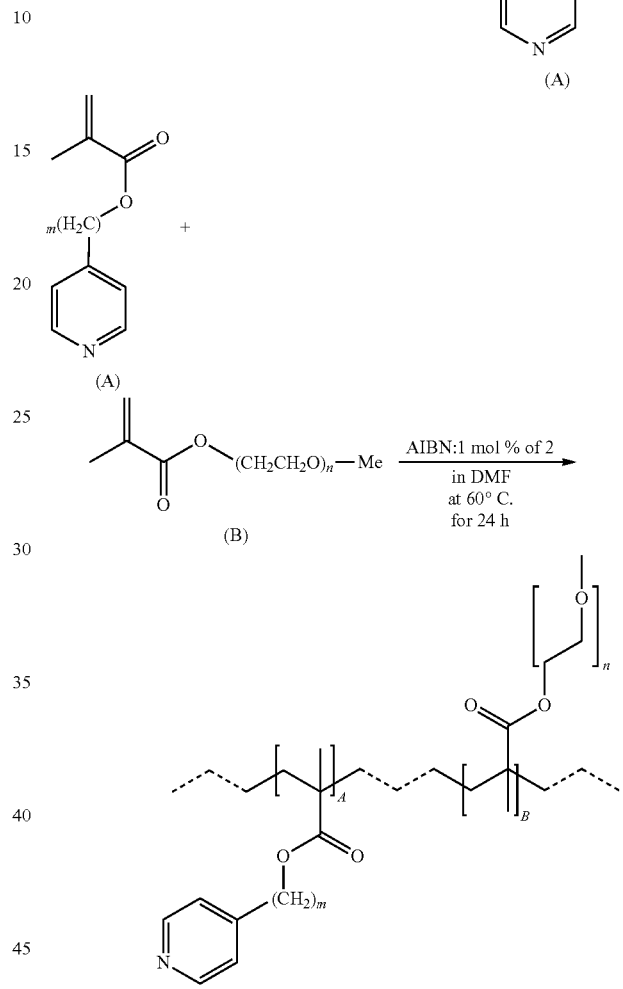

Synthesis of Polymerizable Monomer (A) (m=3)
(Synthesis Example 1)

After 6.85 g (50 mmol) of 4-pyridinepropanol, 4.73 g (55 mmol) of methacrylic acid, and 740 mg (5 mmol) of 4-(1-pyrrolidinyl)pyridine were dissolved in 100 ml of anhydrous dichloromethane, 11.3 g (55 mmol) of N,N'-dicyclohexylcarbodiimide (DCC) was added thereto and allowed to react at room temperature for 1 hour. Insoluble urea was removed by filtration, followed by removing solvent under reduced pressure. The residual material was purified by column chromatography (column: silica, solvent: hexane/ethyl acetate) to obtain 8.5124 g (41.4 mmol) of the polymerizable monomer (A) of colorless oil (yield rate: 82.8%).

Synthesis of Py-g-PEG
(Synthesis Example 2)

After 205 mg (10 mmol) of 4-pyridinepropanol-methacrylate of the polymerizable monomer (A) of the present invention resulting from Synthesis Example 1, 208 mg (0.1 mmol) of α-methyl-ω-methacryloyl-polyethylene glycol of the polymerizable monomer (B) of the present invention, and AIBN of 1% by mass of 4-pyridinepropanol-methacrylate were dissolved in DMF (4 ml), the solution was subjected to 3 cycles of freeze-degassing, followed by allowing to react at 60° C. for 24 hours. The reaction liquid was added dropwise into a reprecipitation solvent (isopropyl alcohol/diethyl ether=1/20 in volume ratio) in 20 times amount of DMF, then which was stirred for several minutes. Subsequently, 202 mg (1.8 µmol) of Py-g-PEG of white powder was obtained through centrifugal separation and freeze dehydration (yield rate: 49%). Number-average molecular weight (Mn) of the resulting Py-g-PEG was 113,180, dispersion degree (Mw/Mn) was 1.634, and copolymerization ratio (PEG/Py) of polyethylene glycol (PEG) to pyridine (Py) was 10.3%. Here, the molecular weight was measured by gel permeation chromatography (GPC).

Preparation of Au—Ag Core-Shell Nanorod Particles Protected by Py-g-PEG

Preparation of CTAB-Protected Gold Nanorod Particles

Hexadecyltrimethylammonium bromide (CTAB) protected gold nanorod particles were prepared in accordance with Seed process. To a mixed solution of 2.5 ml of 0.1 M CTAB solution and 2.5 ml of 1 mM chloroauric acid ($HAuCl_4$) solution, 0.3 ml of 10 mM sodium borohydride ($NaBH_4$) solution in an ice bath was added, then which was stirred for 5 minutes to obtain a gold seed dispersion. Next, to a mixed solution of 50 ml of 0.1 M CTAB solution and 4.5 ml of 1 mM silver nitrate ($AgNO_3$) solution, 50 ml of 0.5 mM $HAuCl_4$ solution was added, then which was stirred for 30 minutes, followed by further adding 2.5 ml of 0.01 M ascorbic acid aqueous solution. To this solution, 2.5 ml of the gold seed dispersion was added, then which was stirred in a constant-temperature bath at 25° C. for one day, thereby obtaining a dispersion of CTAB-protected gold nanorod particles.

Preparation of Py-g-PEG Protected Gold Nanorod Particles

The dispersion of CTAB-protected gold nanorod particles resulting from the process described above was centrifuged (rotation speed: 21,000 rpm, period: 30 minutes, times: once) using an ultracentrifuge (Optima TLX, by Beckman Coulter Inc.), thereby obtaining a precipitate. Next, the Py-g-PEG resulting from Synthesis Example 2 was dissolved in 20 ml of water to obtain a Py-g-PEG solution. Then, the precipitate was re-dispersed using the Py-g-PEG solution (total amount: 10 ml) so that the concentration became 0.5 mg/ml, then which was stirred in a constant-temperature bath at 25° C. for 2 days, followed by dialysis for 2 days in a dialysis membrane (molecular weight cut off: about 10,000) using 3,000 ml of water. The dialyzed dispersion was centrifuged (rotation speed: 21,000 rpm, period: 30 minutes, times: twice) using the ultracentrifuge, then the resulting precipitate was re-dispersed into sterile water so that the total amount became 100 ml, thereby obtaining a dispersion of Py-g-PEG protected gold nanorod particles.

Deposition of Ag on Surface of Py-g-PEG Protected Gold Nanorod Particles

To 5 ml of the dispersion of Py-g-PEG protected gold nanorod particles resulting from the process described above, 1 mM $AgNO_3$ solution was added (60 µl, 120 µl, 240 µl, 360 µl). To these solutions, 0.1 ml of 0.1 M ascorbic acid aqueous solution was added and then 0.2 ml of 0.1 M NaOH aqueous solution was added. Subsequently, they were stirred in a constant-temperature bath at 25° C. for one day, followed by dialysis for 3 days in a dialysis membrane (molecular weight cut off: about 10,000) using 3,000 ml of water. The dialyzed solutions were centrifuged (rotation speed: 18,000 rpm, period: 30 minutes, times: once) using the ultracentrifuge, then the resulting precipitates were re-dispersed into sterile water so that the total amount became 100 ml, thereby obtaining dispersions of Py-g-PEG protected gold nanorod particles.

Measurement of Plasmon Absorption of Dispersion of Py-g-PEG Protected Gold Nanorod Particles In general, metal nanoparticles with a size region of several 10 nm exhibit characteristic optical absorption derived from surface plasmon excitation depending on species, shape, etc. of the metal. For example, it is known that dispersions of spherical gold nanoparticles exhibit absorption around 520 nm, while those of rod shape exhibit absorption at a side of longer wavelength (around 900 nm) derived from long axis of the rod in addition to the absorption around 520 nm derived from short axis of the rod. Plasmon absorption was measured for the dispersions of Py-g-PEG protected gold nanorod particles resulting from the process described above by a spectral photometer (Agilent 8453A Diod Array, by Agilent Co.); consequently, large absorption around 900 nm was recognized in addition to the absorption around 520 nm (FIG. 1). Furthermore, there was displayed a red color specific for gold nanoparticles in the dispersions of Py-g-PEG protected gold nanorod particles.

Figure 2:
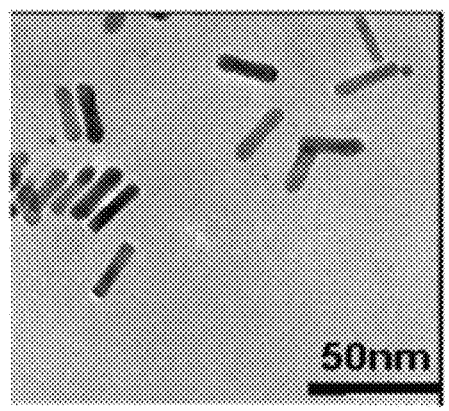
FIG. 2 is a transmission electron microscope (TEM) image of Py-g-PEG protected gold nanorod particles.

Measurement of Particle Size and Confirmation of Shape of Py-g-PEG Protected Gold Nanorod Particles Particle size of the Py-g-PEG protected gold nanorod particles resulting from the process described above was measured by a dynamic light scattering photometer (DLS, DLS-7000, manufactured by Otsuka Electronics Co.). Particle size and shape of the particles were also observed by a transmission electron microscope (TEM, HITACHI H-9500, manufactured by Hitachi High-Technologies Co.). As a result, a rod shape with an average particle size of short axis 9.5±2 nm and long axis 40.9±4.5 nm was confirmed (FIG. 2).

Figure 5:
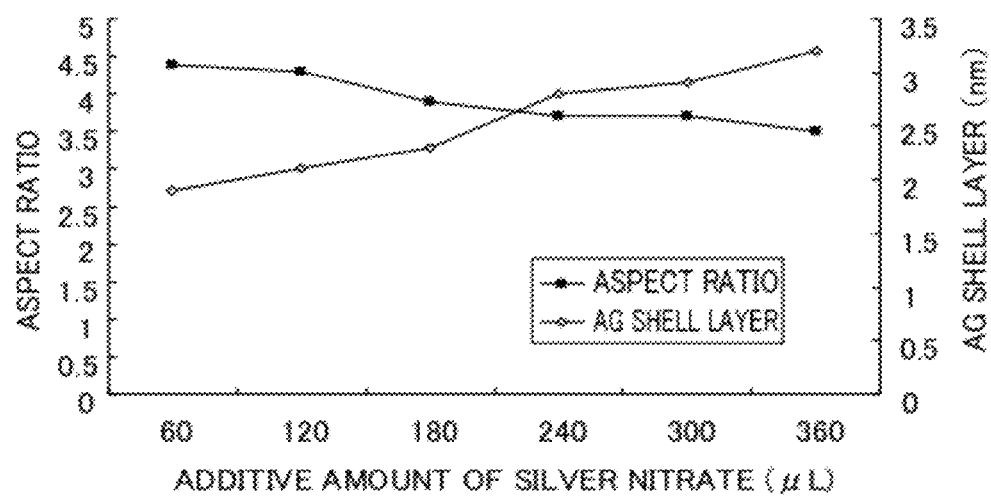
FIG. 5 is a view that shows aspect ratio of long axis to short axis of Py-g-PEG protected Au—Ag core-shell nanorod particles.

Measurement of Plasmon Absorption of Dispersion of Py-g-PEG Protected Au—Ag Core-Shell Nanorod Particles Plasmon absorption was measured for the dispersions of Py-g-PEG protected Au—Ag core-shell nanorod particles resulting from the process described above by the spectral photometer; consequently, shift to the side of Ag-specific plasmon absorption wavelength (around 400 nm) and increase of absorption were recognized as the deposition amount of silver increased (FIG. 3). It is believed that plasmon absorption increased due to formation of a shell layer by silver deposition since the Ag-specific plasmon absorption is larger than that of Au. Furthermore, the color of the dispersions of Py-g-PEG protected Au—Ag core-shell nanorod particles changed from red to blue as the deposition amount of silver increased. Measurement of Particle Size and Confirmation of Shape of Py-g-PEG Protected Au—Ag Core-Shell Nanorod Particles Shape of the Py-g-PEG protected Au—Ag core-shell nanorod particles resulting from the process described above was observed by TEM; consequently, formation of a shell layer of silver was confirmed around the gold nanorod. Furthermore, particle size of particles and thickness of the shell layer of silver were measured by TEM and then an aspect ratio of long axis to short axis (long axis/short axis) was determined; consequently, it was confirmed that the shape of particles approached to a spherical shape as the deposition amount of silver increased (FIGS. 4, 5).

Preparation of Au—Ag Core-Shell Nanorod Particles Protected by SH-PEG

Preparation of CTAB-Protected Nanorod Particles

CTAB-protected gold nanorod particles were also prepared in accordance with Seed process. To a mixed solution of 2.5 ml of 0.1 M CTAB solution and 2.5 ml of 1 mM $HAuCl_4$ solution, 0.3 ml of 10 mM $NaBH_4$ solution in an ice bath was added, then which was stirred for 5 minutes to obtain a gold seed dispersion. Next, to a mixed solution of 50 ml of 0.1 M CTAB solution and 4.5 ml of AgNO$_3$ solution, 50 ml of 0.5 mM HAuCl$_4$ solution was added, then which was stirred for 30 minutes, followed by further adding 2.5 ml of 0.01 M ascorbic acid aqueous solution. To this solution, 2.5 ml of the gold seed dispersion was added, then which was stirred in a constant-temperature bath at 25° C. for one day, thereby obtaining a dispersion of CTAB-protected gold nanorod particles.

Preparation of SH-PEG Protected Gold Nanorod Particles

The dispersion of CTAB-protected gold nanorod particles resulting from the process described above was centrifuged (rotation speed: 21,000 rpm, period: 30 minutes, times: once) using the ultracentrifuge, thereby obtaining a precipitate. Next, SH-PEG (end-thiolated polyethylene glycol, 2M4E0H01) was dissolved in 100 ml of water to obtain a SH-PEG solution. Then, the precipitate was re-dispersed using the SH-PEG solution so that the concentration became 0.5 mg/ml, then which was stirred in a constant-temperature bath at 25° C. for 2 days, followed by dialysis for 2 days in a dialysis membrane (molecular weight cut off: about 10,000) using 3,000 ml of water. The dialyzed dispersion was centrifuged (rotation speed: 21,000 rpm, period: 30 minutes, times: twice) using the ultracentrifuge, then the resulting precipitate was re-dispersed into sterile water so that the total amount became 100 ml, thereby obtaining a dispersion of SH-PEG protected gold nanorod particles.

Deposition of Silver on Surface of SH-PEG Protected Gold Nanorod Particles

To 5 ml of the dispersion of SH-PEG protected gold nanorod particles resulting from the process described above, 120 μl of 1 mM AgNO$_3$ solution was added. To this dispersion, 0.1 ml of 0.1 M ascorbic acid aqueous solution was added and then 0.2 ml of 0.1 M NaOH aqueous solution was added. Subsequently, it was stirred in a constant-temperature bath at 25° C. for one day, followed by dialysis for 3 days in a dialysis membrane (molecular weight cut off: about 10,000) using 3,000 ml of water. The dialyzed solution was centrifuged (rotation speed: 18,000 rpm, period: 30 minutes, times: once) using the ultracentrifuge, then the resulting precipitate was re-dispersed into sterile water so that the total amount became 100 ml, thereby obtaining a test liquid.

Measurement of Plasmon Absorption

Figure 6:
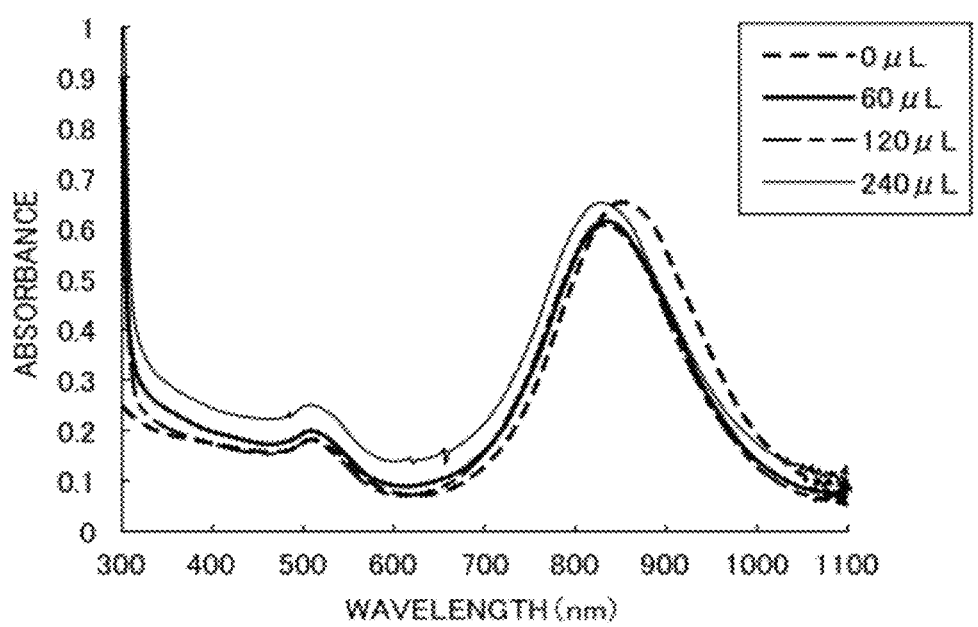
FIG. 6 is a view that shows absorption spectra of a test liquid in which Ag was deposited on the surface of SH-PEG protected gold nanorod particles.

Plasmon absorption was measured for the test liquid resulting from the process described above by the spectral photometer; consequently, shift to the side of Ag-specific plasmon absorption wavelength (around 400 nm) and increase of absorption along with increase of Ag deposition amount were not recognized (FIG. 6). It was confirmed from these facts that no shell layer was formed and thus Au—Ag core-shell nanorod particles could not be formed even by depositing silver on the surface of gold nanorod particles protected by SH-PEG.

Figure 7A:
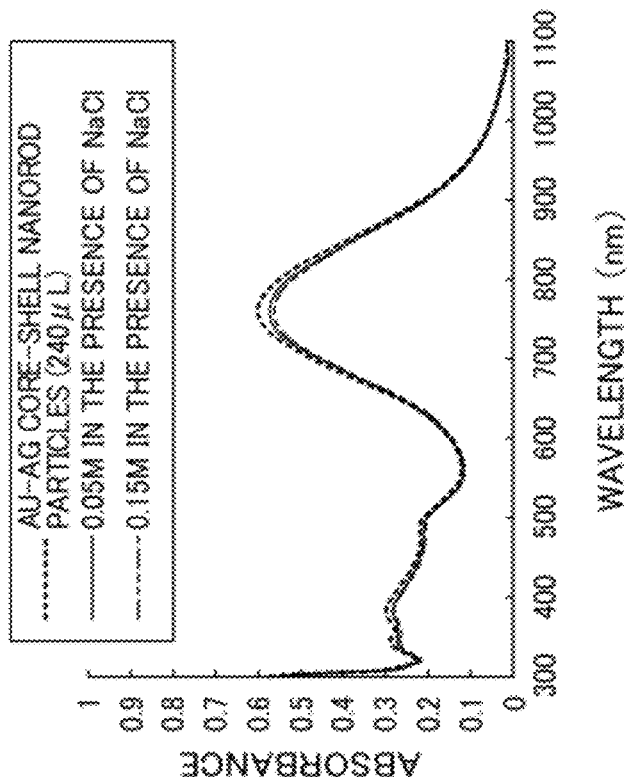
FIG. 7 is a view that shows dispersion stability (in a salt solution) of Py-g-PEG protected Au—Ag core-shell nanorod particles (additive amount of 1 mM $AgNO_3$ solution: (A) 120 μl, (B) 240 μl)
Figure 7B:
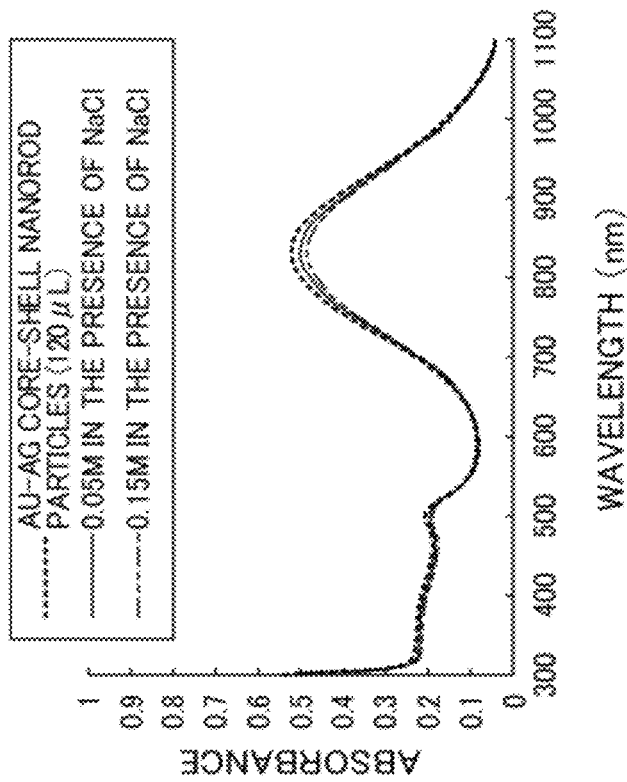

Evaluation of Dispersion Stability of Py-g-PEG Protected Au—Ag Core-Shell Nanorod Particles Dispersion in Salt The dispersions of Py-g-PEG protected Au—Ag core-shell nanorod particles resulting from the process described above (additive amount of 1 mM AgNO$_3$ solution: 120 μl, 240 μl) were centrifuged (rotation speed: 15,000 rpm, period: 30 minutes, times: once) using the ultracentrifuge, thereby obtaining precipitates. Next, a sodium chloride aqueous solution was added to these precipitates so that the concentration became 0.05 M or 0.15 M, then which was re-dispersed, followed by stirring in a constant-temperature bath at 25° C. for 2 days. Then, plasmon absorption was measured for the resulting dispersions by the spectral photometer. As a result, significant change in terms of intensity and position of the plasmon absorption was not recognized for all dispersions (FIG. 7). It was confirmed from these facts that the Py-g-PEG protected Au—Ag core-shell nanorod particles represent high dispersibility with the salt.

Dispersity in 10% FBS containing DMEM

The dispersion of Py-g-PEG protected Au—Ag core-shell nanorod particles resulting from the process described above (additive amount of 1 mM AgNO$_3$ solution: 120 μl) was centrifuged (rotation speed: 15,000 rpm, period: 30 minutes, times: once) using the ultracentrifuge, thereby obtaining a precipitate. Next, 50 ml of DMEM containing 10% of fetal bovine serum (FBS) was added to the precipitate, then which was re-dispersed. Then, plasmon absorption was measured with time for the dispersion by the spectral photometer. As a result, decrease of absorbance and shift of maximum absorption wavelength due to agglomeration were not recognized at all (FIG. 8). It was confirmed from these facts that the Py-g-PEG protected Au—Ag core-shell nanorod particles showed very stable dispersibility in the serum.

Figure 9:
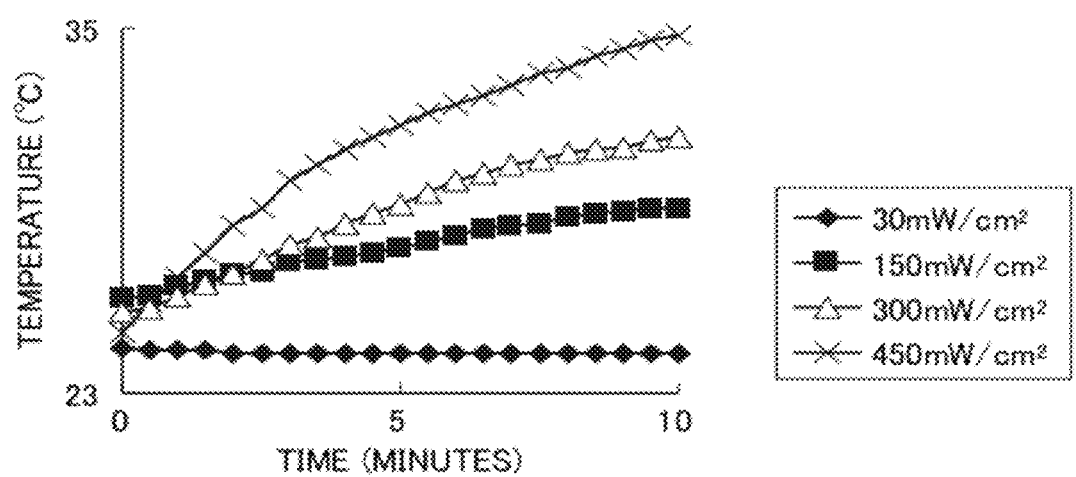
FIG. 9 is a view that shows an evaluation result of a photothermal effect of Py-g-PEG protected Au—Ag core-shell nanorod particles (dependency on laser intensity)

Evaluation of Photothermal Effect of Py-g-PEG Protected Au—Ag Core-Shell Nanorod Particles Dependency on Laser Intensity Using the dispersion of Py-g-PEG protected Au—Ag core-shell nanorod particles resulting from the process described above (additive amount of 1 mM AgNO$_3$ solution: 480 μl), a dispersion with a particle concentration of 96 μg/ml was prepared. The prepared liquid was introduced into a plastic cell of 1 cm, then which was irradiated with laser light of 800 nm (irradiation energy: 30 mW/cm$^2$, 150 mW/cm$^2$, 300 mW/cm$^2$, 450 mW/cm$^2$, irradiated area: 1 mm$^2$) using an OPO laser (SL454G pulsed Nd:YAG laser, manufactured by Spectron Laser System). During the experiment of laser irradiation, Signal light or Idler light was cut using a cut filter. The output laser light was converged using a lens (SLB-30-50PM, spherical plano-convex lens, manufactured by Sigma Koki Co.). Here, the cells were within the constant-temperature bath at 25° C. until just before irradiation of laser light in order to stabilize an initiation temperature. As a result, it was confirmed that the photothermal effect of Py-g-PEG protected Au—Ag core-shell nanorod particles depends on laser intensity (FIG. 9).

Dependency on Particle Concentration

Figure 10:
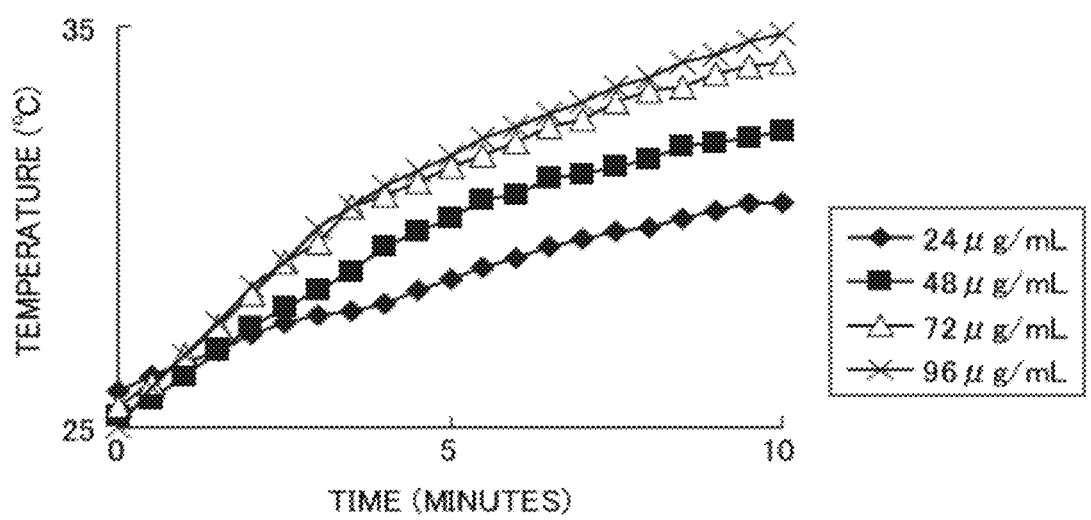
FIG. 10 is a view that shows an evaluation result of a photothermal effect of Py-g-PEG protected Au—Ag core-shell nanorod particles (dependency on particle concentration)

Using the dispersion of Py-g-PEG protected Au—Ag core-shell nanorod particles resulting from the process described above (additive amount of 1 mM AgNO$_3$ solution: 240 μl), dispersions with a particle concentration of 24 μg/ml, 48 μg/ml, 72 μg/ml, or 96 μg/ml were prepared. The prepared liquids were introduced into plastic cells of 1 cm, then which were irradiated with laser light of 800 nm (irradiation energy: 450 mW/cm$^2$, irradiated area: 1 mm$^2$) using the OPO laser (SL454G pulsed Nd:YAG laser, manufactured by Spectron Laser System). During the experiment of laser irradiation, Signal light or Idler light was cut using a cut filter. The output laser light was converged using the lens (SLB-30-50PM, spherical plano-convex lens, manufactured by Sigma Koki Co.). Here, the cells were kept within the constant-temperature bath at 25° C. until just before irradiation of laser light in order to stabilize an initiation temperature. As a result, it was confirmed that the photothermal effect of Py-g-PEG protected Au—Ag core-shell nanorod particles depends on particle concentration (FIG. 10).

Comparison with Gold Nanorod Particles (1)

Figure 11:
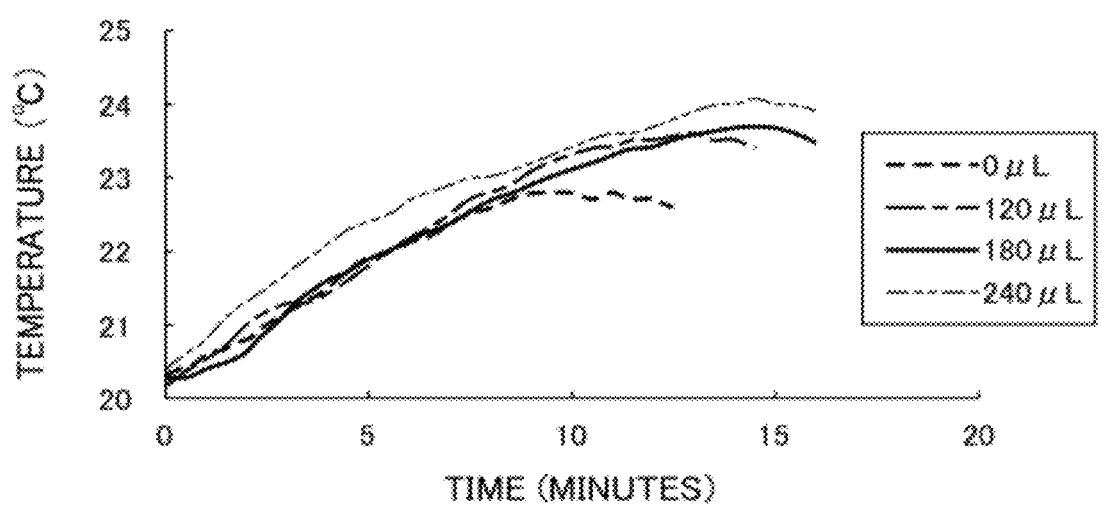
FIG. 11 is a view that shows an evaluation result of a photothermal effect of Py-g-PEG protected Au—Ag core-shell nanorod particles (comparison with gold nanorod particles (1))

It is known that gold nanorod particles exhibit a photothermal effect to convert absorbed optical energy into heat upon irradiation with near-infrared light. So, the photothermal effect was compared between the dispersion of Py-g-PEG protected gold nanorod particles resulting from the process described above (additive amount of 1 mM AgNO₃ solution: 0 μl) and the dispersions of Py-g-PEG protected Au—Ag core-shell nanorod particles resulting from the process described above (additive amount of 1 mM AgNO₃ solution: 120 μl, 180 μl, 240 μl). Each of 2 ml of the dispersions was introduced into a plastic cell of 1 cm and induced to generate third harmonics (355 nm) of an excitation light source using the OPO laser (SL454G pulsed Nd:YAG laser, manufactured by Spectron Laser System). The laser light was turned to wavelength-variable laser light by changing an angle of BBO-type nonlinear optical crystal (β-BaB₂O₄) in a midband OPO VisIR2 device (manufactured by GWU Lasertechnik). Here, repeating frequency was 10 Hz and pulse width was 2-3 ns. The device is capable of outputting over a wide wavelength region of 400 to 2,200 nm. During the experiment of laser irradiation, Signal light or Idler light was cut using a cut filter. The output laser light was converged using the lens (SLB-30-50PM, spherical plano-convex lens, manufactured by Sigma Koki Co.). Laser light of 800 nm was irradiated (irradiation energy: 0.5 mW/cm²·pulse, irradiated area: 1 mm²). Here, the cells were kept within the constant-temperature bath at 20° C. until just before irradiation of laser light in order to stabilize an initiation temperature. As a result, it was confirmed that the photothermal effect of Py-g-PEG protected Au—Ag core-shell nanorod particles is higher than that of Py-g-PEG protected gold nanorod particles (FIG. 11). It is believed that the photothermal effect is enhanced by coating with silver since silver-specific plasmon absorption is larger than that of gold.

Comparison with Gold Nanorod Particles (2)

Figure 12:
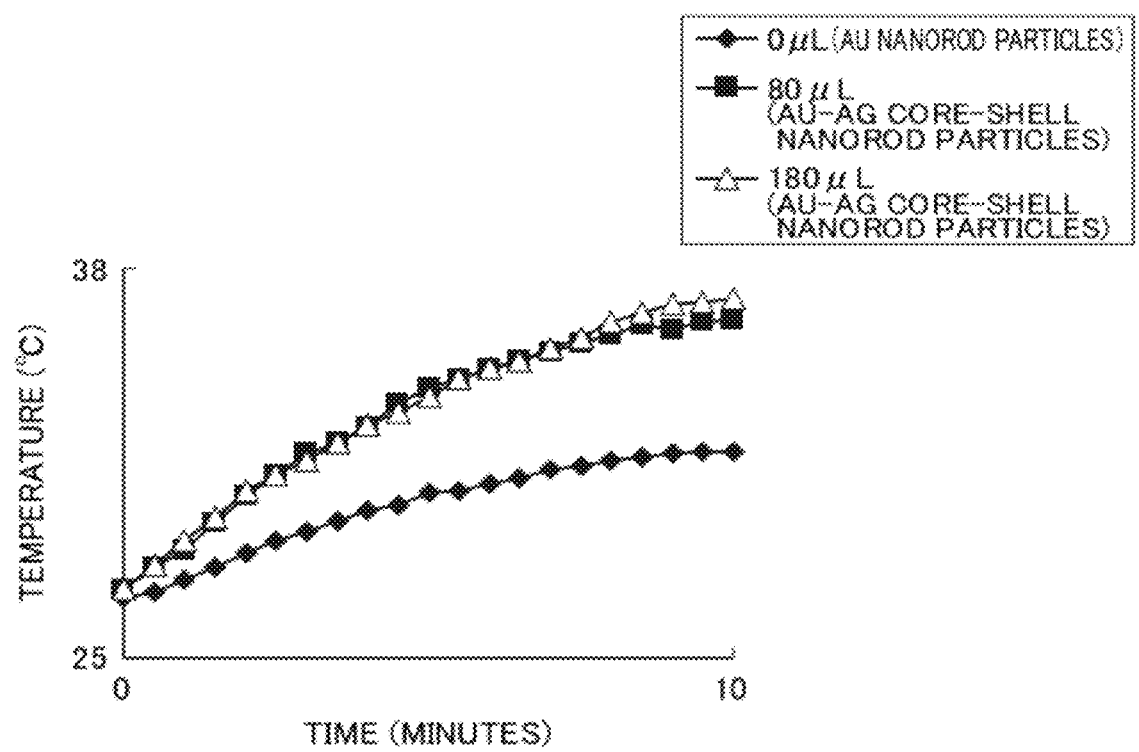
FIG. 12 is a view that shows an evaluation result of a photothermal effect of Py-g-PEG protected Au—Ag core-shell nanorod particles (comparison with gold nanorod particles (2))

Next, the Py-g-PEG protected gold nanorod particles resulting from the process described above and the gold nanorod particles were compared with respect to the photothermal effect while changing the irradiation energy of laser light and the initiation temperature of the cells. The dispersion of Py-g-PEG protected gold nanorod particles resulting from the process described above (additive amount of 1 mM AgNO₃ solution: 0 μl) and the dispersions of Py-g-PEG protected Au—Ag core-shell nanorod particles resulting from the process described above (additive amount of 1 mM AgNO₃ solution: 80 μl, 180 μl) were used as samples to be measured. Then, they were compared by the same process as that of Comparison with Gold Nanorod Particles (1) described above except that irradiation energy of the laser light of 800 nm was 450 mW/cm² and the temperature of the constant-temperature bath in which the cells were kept was 25° C. As a result, it was definitely demonstrated that the photothermal effect of Py-g-PEG protected Au—Ag core-shell nanorod particles is higher than that of Py-g-PEG protected gold nanorod particles (FIG. 12).

Synthesis of Block Copolymer

As shown in the reaction scheme below, the polymerizable monomer (A) and the polymerizable monomer (B) were copolymerized to synthesize a block copolymer (Py-b-PEG).

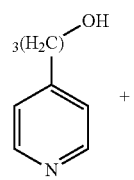

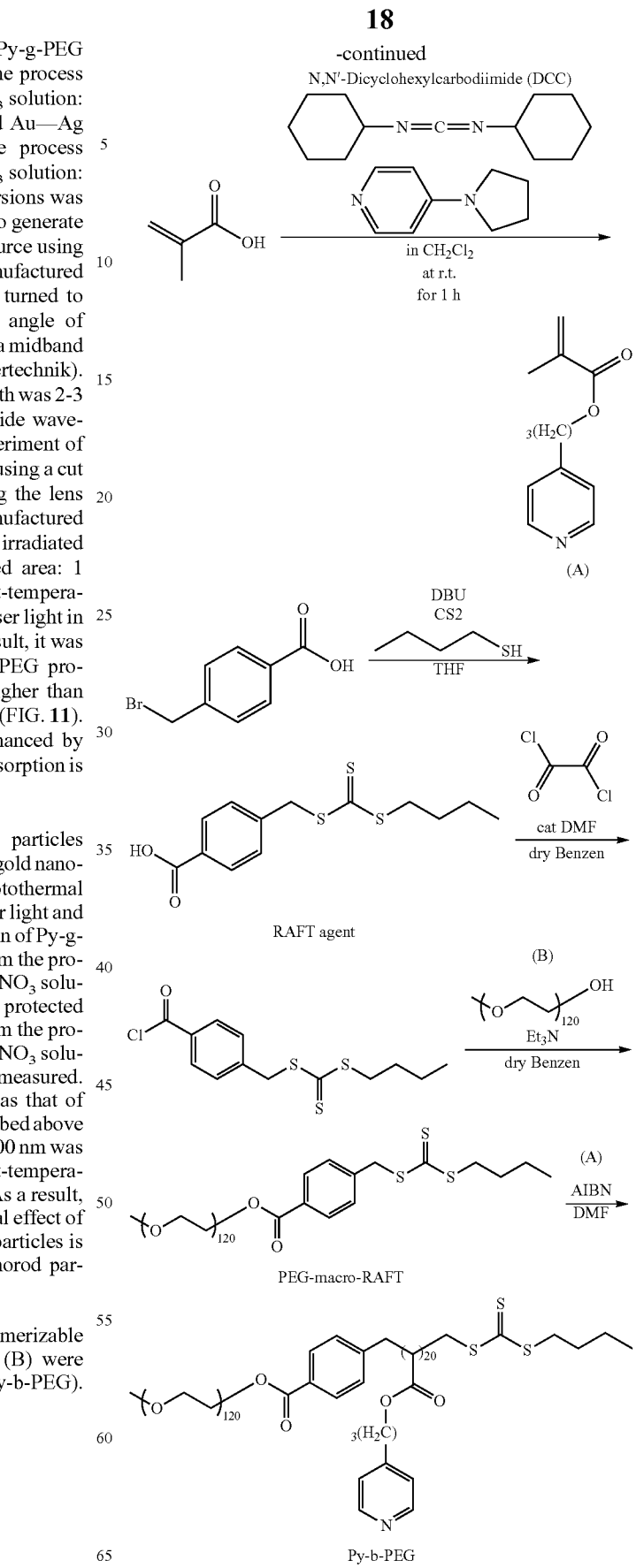

Synthesis of RAFT Agent
(Synthesis Example 3)

Three grams (13.95 mmol) of 4-bromomethylbenzoic acid was dissolved in 25 ml of tetrahydrofuran to obtain a tetrahydrofuran solution of 4-bromomethylbenzoic acid. Next, under argon atmosphere, 1.80 ml (16.74 mmol, 1.2 equivalents to 4-bromomethylbenzoic acid) of 1-butane thiol, 2.5 ml (16.74 mmol, 1.2 equivalents to 4-bromomethylbenzoic acid) of diazabicycloundecene, and 1.01 ml (16.74 mmol, 1.2 equivalents to 4-bromomethylbenzoic acid) of carbon bisulfide were added to 75 ml of dehydrated tetrahydrofuran, then which was stirred at room temperature for 30 minutes. After stirring, the tetrahydrofuran solution of 4-bromomethylbenzoic acid was added dropwise thereto, then which was further stirred for 6 hours. Progress of the reaction was confirmed by TLC, and it was dissolved in benzene after Celite filtration and condensation. It was further subjected to rinsing with 1 M HCl and ion-exchange water, and dewatering treatment using anhydrous magnesium sulfate, followed by condensation and freeze drying, thereby obtaining a RAFT agent (yield amount: 3.78 g, yield rate: 93.9%).

Synthesis of Monomer (B)-Macro-RAFT Agent
(Synthesis Example 4)

Under argon atmosphere, 720 mg (2.4 mmol, 10 equivalents to the monomer (B) described later) of the RAFT agent resulting from Synthesis Example 3 was dissolved in anhydrous benzene, then to which 242 µl (2.88 mmol, 1.2 equivalents to the RAFT agent) of oxalyl chloride and a small amount of N,N-dimethylformamide (cat.) were added and stirred, followed by confirming generation of an acid chloride by TLC and then condensing thereof. Next, the acid chloride was dissolved in 7 ml of anhydrous benzene, then to which 400 µl (2.88 mmol, 1.2 equivalents to the RAFT agent) of triethylamine dissolved in anhydrous benzene and 1200 mg (0.24 mmol) of polyethylene glycol (PEG) (5K) as a monomer (B) of the present invention were added, followed by stirring in an oil bath at 70° C. overnight. Subsequently, it was subjected to Celite filtration and condensation, followed by reprecipitation using 20 times amount of isopropyl ether. The resulting precipitate was dissolved in chloroform, then which was freeze-dried after condensation, thereby obtaining a PEG-macro-RAFT agent where the RAFT agent is introduced into an end of the polymer resulting from polymerization of the monomer (B) (yield amount: 1,060 mg, yield rate: 83.3%, end modification rate: 85%).

Synthesis of Py-b-PEG
(Synthesis Example 5)

Two hundred mg (0.062 mmol) of the PEG-macro-RAFT agent resulting from Synthesis Example 4 and 250 mg (1.2 mmol, 20 equivalents to the PEG-macro-RAFT agent) of 4-pyridinepropanol-methacrylate as a polymerizable monomer (A) of the present invention resulting from Synthesis Example 1 were dissolved in 3 ml of N,N-dimethylformamide and introduced into a polymerization tube, then 3.0 mg (0.018 mmol, 0.3 equivalents to the PEG-macro-RAFT agent) of AIBN was further added thereto. It was then subjected to 3 cycles of freeze-degassing and flushing with argon gas, followed by stirring in an oil bath at 70° C. for 3 days. Subsequently, it was subjected to Celite filtration and condensation, followed by twice reprecipitation using 20 times amount of isopropyl ether. The resulting precipitate was freeze-dried, thereby obtaining Py-b-PEG (yield amount: 369 mg, yield rate: 82%). In regards to the resulting Py-b-PEG, theoretical number-average molecular weight (Mw(th)) was 5,530, polydispersity (Mw/Mn) was 0.2878, and copolymer ratio of PEG-macro-RAFT agent and Py and AIBN (PEG-macro-RAFT agent/Py/AIBN) was 1/20/0.2. Furthermore, particle size distribution (histogram particle size) was 28.0±18.0 nm, and average particle size (cumulative particle size) was 19.2 nm. Here, the theoretical number-average molecular weight was calculated from a chain number of Py chain based on ethylene oxide chain of PEG by $^1$H-NMR. The particle size distribution (histogram particle size), the average particle size (cumulative particle size), and the polydispersity (Mw/Mn) were calculated from dynamic light scattering.

Preparation of Py-b-PEG Protected Gold Nanorod Particles

The dispersion of CTAB-protected gold nanorod particles resulting from the process described above was centrifuged (rotation speed: 21,000 rpm, period: 30 minutes, times: once) using the ultracentrifuge (Optima TLX, by Beckman Coulter Inc.), thereby obtaining a precipitate. Next, the Py-b-PEG resulting from Synthesis Example 5 was dissolved in 20 ml of water to obtain a Py-b-PEG solution. Then, the precipitate was re-dispersed using the Py-b-PEG solution (total amount: 10 ml) so that the concentration became 0.5 mg/ml, then which was stirred in a constant-temperature bath at 25° C. for 2 days, followed by dialysis for 2 days in a dialysis membrane (molecular weight cut off: about 10,000) using 3,000 ml of water. The dialyzed dispersion was centrifuged (rotation speed: 21,000 rpm, period: 30 minutes, times: twice) using the ultracentrifuge, then the resulting precipitate was re-dispersed into sterile water so that the total amount became 100 ml, thereby obtaining a dispersion of Py-b-PEG protected gold nanorod particles.

Deposition of Ag on Surface of Py-b-PEG Protected Gold Nanorod Particles

To 5 ml of the dispersion of Py-b-PEG protected gold nanorod particles resulting from the process described above, 1 mM $AgNO_3$ solution was added (120 µl, 240 µl, 360 µl, 480 µl). To these solutions, 0.1 ml of 0.1 M ascorbic acid aqueous solution was added and then 0.2 ml of 0.1 M NaOH aqueous solution was added. Subsequently, they were stirred in a constant-temperature bath at 25° C. for one day, followed by dialysis for 3 days in a dialysis membrane (molecular weight cut off: about 10,000) using 3,000 ml of water. The dialyzed dispersion was centrifuged (rotation speed: 18,000 rpm, period: 30 minutes, times: once) using the ultracentrifuge, then the resulting precipitate was re-dispersed into sterile water so that the total amount became 100 ml, thereby obtaining a dispersion of Py-b-PEG protected Au—Ag core-shell nanorod particles.

Figure 13:
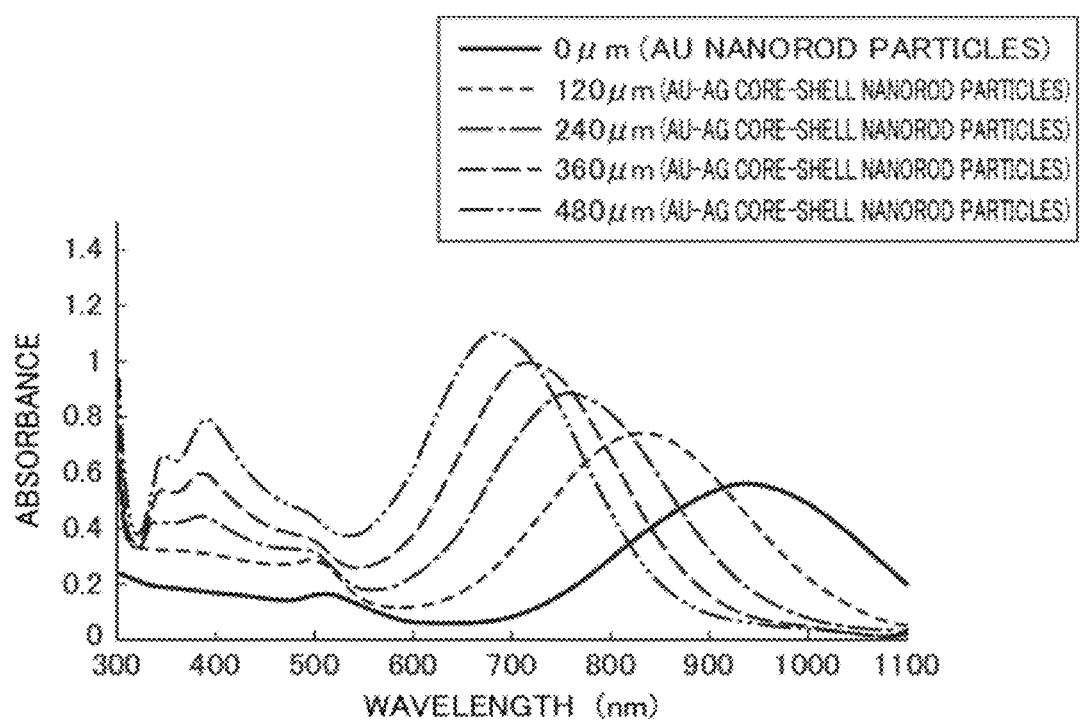
FIG. 13 is a view that shows absorption spectra of a dispersion of Py-b-PEG protected Au—Ag core-shell nanorod particles.
Figure 14A:
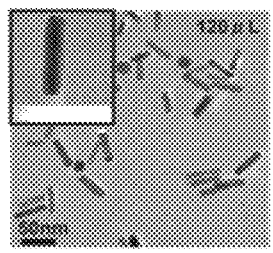
FIG. 14 is a view of Py-b-PEG protected Au—Ag core-shell nanorod particles observed by a transmission electron microscope (TEM) (additive amount of 1 mM $AgNO_3$ solution: (A) 120 μl, (B) 240 μl, (C) 360 μl, (D) 480 μl)
Figure 14B:
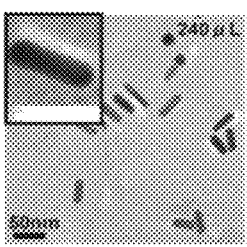
Figure 14C:
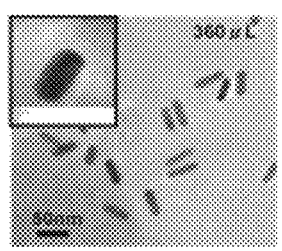
Figure 14D:
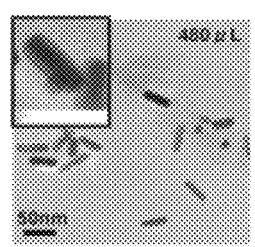

Measurement of Plasmon Absorption of Dispersion of Py-b-PEG
Protected Au—Ag Core-Shell Nanorod Particles Plasmon absorption was measured for the dispersions of Py-g-PEG protected Au—Ag core-shell nanorod particles resulting from the process described above by the spectral photometer; consequently, shift to the side of Ag-specific plasmon absorption wavelength (around 400 nm) and increase of absorption were recognized as the deposition amount of silver increased (FIG. 13). It is believed that plasmon absorption increased due to formation of a shell layer by silver deposition since the Ag-specific plasmon absorption is larger than that of Au. Furthermore, the color of the dispersions of Py-b-PEG protected Au—Ag core-shell nanorod particles changed from yellow to blue as the deposition amount of silver increased.

Confirmation of Shape of Py-b-PEG Protected Au—Ag Core-Shell Nanorod Particles

Shape of the Py-g-PEG protected Au—Ag core-shell nanorod particles resulting from the process described above was observed by the transmission electron microscope (TEM, HITACHI H-9500, manufactured by Hitachi High-Technologies Co.); consequently, it was confirmed that a shell layer of silver had been formed around gold nanorod (FIG. 14).

Evaluation of Cell Cytotoxicity of Py-g-PEG Protected Au—Ag Core-Shell Nanorod Particles Preparation of Au—Ag Core-Shell Nanorod Particles Protected by Py-g-PEG To 5 ml of the dispersion of Py-g-PEG protected gold nanorod particles resulting from the process described above, 1 mM $AgNO_3$ solution was added (60 µl, 120 µl, 180 µl, 240 µl, 300 µl, 360 µl). To these dispersions, 0.1 ml of 0.1 M ascorbic acid aqueous solution was added and then 0.2 ml of 0.1 M NaOH aqueous solution was added. Subsequently, they were stirred in a constant-temperature bath at 25° C. for one day, followed by dialysis for 3 days in a dialysis membrane (molecular weight cut off: about 10,000) using 3,000 ml of water. The dialyzed dispersion was centrifuged (rotation speed: 18,000 rpm, period: 30 minutes, times: once) using the ultracentrifuge, then the resulting precipitate was re-dispersed into sterile water so that the total amount became 50 ml, thereby obtaining dispersions of Py-g-PEG protected Au—Ag core-shell nanorod particles with a concentration of 8.5 µg/ml, 11.3 µg/ml, 17 µg/ml, 22.6 µg/ml, 34 µg/ml, 50 µg/ml, or 60 µg/ml.

Preparation of Au—Ag Core-Shell Nanorod Particles Protected by CTAB

To 5 ml of the dispersion of CTAB-protected gold nanorod particles resulting from the process described above, 1 mM $AgNO_3$ solution was added (60 µl, 120 µl, 180 µl, 240 µl, 300 µl, 360 µl). To these dispersions, 0.1 ml of 0.1 M ascorbic acid aqueous solution was added and then 0.2 ml of 0.1 M NaOH aqueous solution was added. Subsequently, they were stirred in a constant-temperature bath at 25° C. for one day, followed by dialysis for 3 days in a dialysis membrane (molecular weight cut off: about 10,000) using 3,000 ml of water. The dialyzed dispersion was centrifuged (rotation speed: 18,000 rpm, period: 30 minutes, times: once) using the ultracentrifuge, then the resulting precipitate was re-dispersed into sterile water so that the total amount became 50 ml, thereby obtaining dispersions of CTAB-protected Au—Ag core-shell nanorod particles with a concentration of 8.5 µg/ml, 11.3 µg/ml, 17 µg/ml, 22.6 µg/ml, or 34 µg/ml.

Figure 15B:
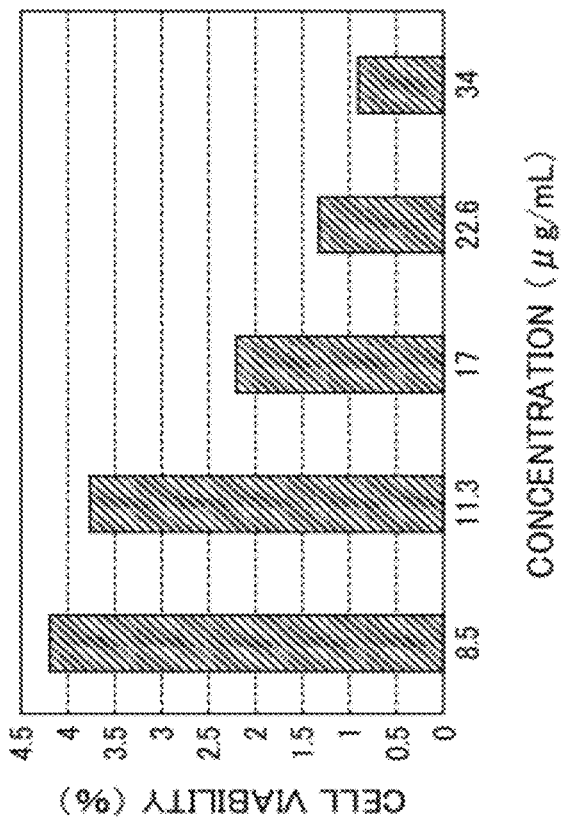
FIG. 15 is a view that shows an evaluation result of cell cytotoxicity ((A) Py-g-PEG protected Au—Ag core-shell nanorod particles, (B) CTAB-protected Au—Ag core-shell nanorod particles)
Figure 15A:
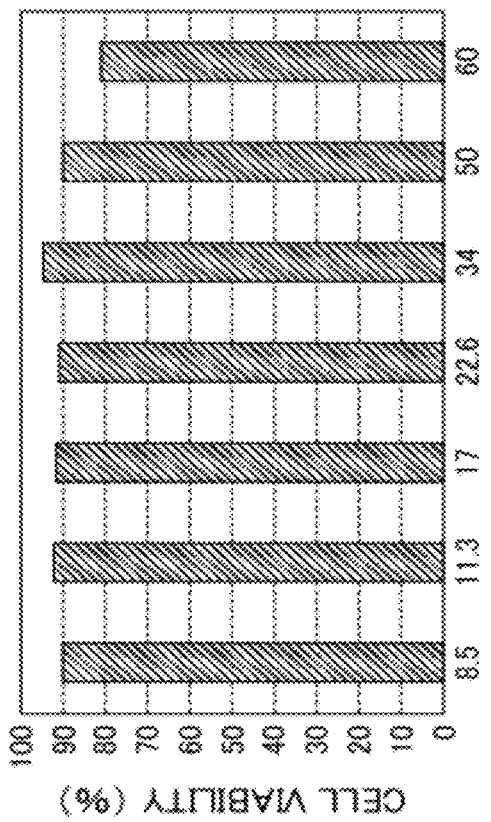

The dispersions of Py-g-PEG protected Au—Ag core-shell nanorod particles resulting from the process described above and the dispersions of CTAB-protected Au—Ag core-shell nanorod particles resulting from the process described above were used for evaluation. Each of 20 ml of the dispersions was centrifuged (rotation speed: 18,000 rpm, period: 30 minutes, times: once) using the ultracentrifuge, then the resulting precipitate was added with DMEM containing 10% of fetal bovine serum (FBS) and re-dispersed so that the total amount became 50 ml. Next, the re-dispersed liquid was purified by a filter (Millex-GV filter, 0.22 µm, manufactured by Millipore Co.) To 0.5 ml of each of purified re-dispersed liquids, HeLa cells (cell number: $5 \times 10^4$) were added, then which was incubated at 37° C. for 30 minutes. Then, cell cytotoxicity was evaluated using a cell growth measuring kit (MTT, manufactured by Calbiochem Novabiochem Novagen). As a result, it was confirmed that the dispersions of CTAB-protected Au—Ag core-shell nanorod particles are highly toxic to cells. On the other hand, it was confirmed that the dispersions of Py-g-PEG protected Au—Ag core-shell nanorod particles of the present invention do not show toxicity to cells (FIG. 15).

Cell Uptake of Py-g-PEG Protected Au—Ag Core-Shell Nanorod Particles

A dispersion of Au—Ag core-shell nanorod particles with a particle concentration of 96 µg/ml was obtained by a process similar to the process described above. The dispersion was centrifuged (rotation speed: 18,000 rpm, period: 15 minutes, times: once) to obtain a precipitate. The precipitate was re-dispersed into a Py-g-PEG-FITC solution in which the Py-g-PEG resulting from Synthesis Example 2 was labeled by fluorescein isothiocyanate (FITC) of a fluorochrome (final concentration of Py-g-PEG-FITC: 0.5 mg/ml). After stirring the re-dispersion in a cold dark place for 3 days, it was centrifuged (rotation speed: 18,000 rpm, period: 15 minutes, times: once) to obtain a precipitate. The precipitate was re-dispersed into 10% FBS containing DMEM to obtain re-dispersions with a concentration of Py-g-PEG protected Au—Ag core-shell nanorod particles, labeled by FITC, of 30 µg/ml, 40 µg/ml, 50 µg/ml, or 60 µg/ml.

After the re-dispersions were purified by the filter (Millex-GV filter, 0.22 µm, manufactured by Millipore Co.), HeLa cells (cell number: $2 \times 10^5$) were added to 1 ml of the purified re-dispersions to incubate at 37° C. for 4 hours. Then, after exchanging to fresh 10% FBS containing DMEM, the cells were observed by a phase-contrast microscope (Observer.D1, manufactured by Carl Zeiss Co.) and a fluorescence microscope (Observer.D1, manufactured by Carl Zeiss Co.); consequently, it was confirmed that the Py-g-PEG protected Au—Ag core-shell nanorod particles labeled by FITC had been incorporated into the cells dependently on the concentration of the particles (FIG. 16).

Evaluation of Photothermal Effect of Py-g-PEG Protected Au—Ag Core-Shell Nanorod Particles on Cells A dispersion of Au—Ag core-shell nanorod particles with a particle concentration of 96 µg/ml was obtained by a process similar to the process described above. The dispersion was centrifuged (rotation speed: 18,000 rpm, period: 15 minutes, times: once) to obtain a precipitate. The precipitate was re-dispersed into the Py-g-PEG solution resulting from Synthesis Example 2 (final concentration of Py-g-PEG: 0.5 mg/ml). After stirring the re-dispersion in a cold dark place for 3 days, it was centrifuged (rotation speed: 18,000 rpm, period: 15 minutes, times: once) to obtain a precipitate. The precipitate was re-dispersed into 10% FBS containing DMEM to obtain re-dispersions with a concentration of Py-g-PEG protected Au—Ag core-shell nanorod particles of 60 µg/ml or 100 µg/ml.

Figure 17:
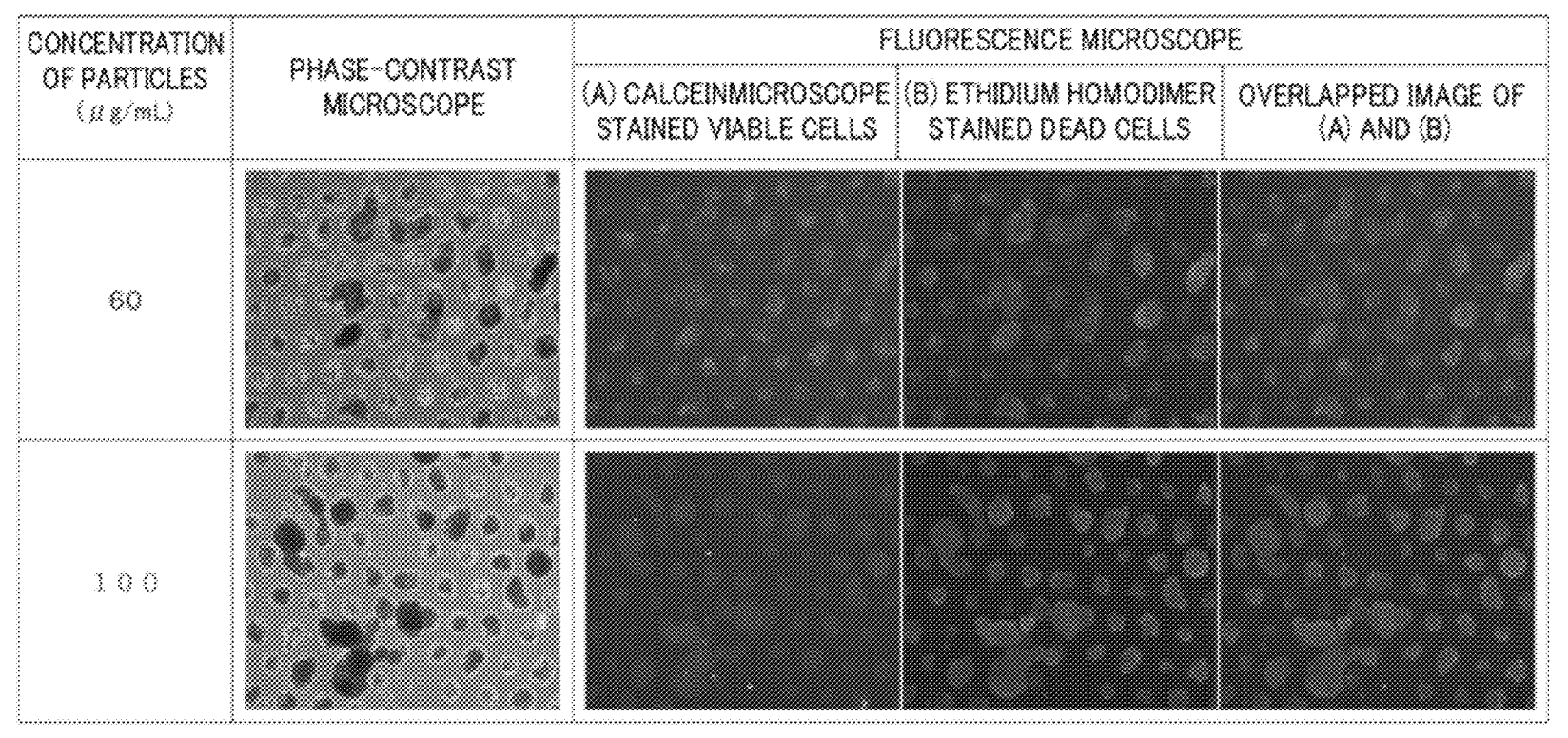

BAEC cells (cell number: $3 \times 10^5$) were seeded on a spheroid-acting microfabricated substrate and incubated for one day, then HepG2 cells (cell number: $5 \times 10^5$) were seeded to form spheroids. To this place, 1 ml of the re-dispersions of Py-g-PEG protected Au—Ag core-shell nanorod particles (particle concentration: 60 µg/ml, 100 µg/ml) was added to incubate at 37° C. for 4 hours, then laser light of 800 nm was irradiated using the OPO laser (SL454G pulsed Nd:YAG laser, manufactured by Spectron Laser System) after exchanging to fresh 10% FBS containing DMEM (irradiation energy: 1,000 mW/cm$^2$, irradiation period: 10 minutes, irradiated area: 1 cm$^2$). Next, after exchanging to fresh 10% FBS containing DMEM again, viable cells stained with calcein AM and dead cells stained with ethidium homodimer were observed by the fluorescence microscope (Observer.D1, manufactured by Carl Zeiss Co.); consequently, it was confirmed that the cells had been killed by the heat that had generated from the Py-g-PEG protected Au—Ag core-shell nanorod particles (FIG. 17).

As described above, it was demonstrated that the Au—Ag core-shell nanorod particles of the present invention exhibit excellent dispersion stability not only in salt solutions but also even in solutions containing sera and have high safety without showing toxicity to cells. Furthermore, the Au—Ag core-shell nanorod particles of the present invention are incorporated into cells and effectively generate heat upon irradiation of light; therefore, application thereof for medical devices for the purpose of photothermal treatment by use of the heat can be anticipated.

The invention claimed is:

1. Au—Ag core-shell nanorod particles, wherein each of the nanorod particles comprises a gold nanorod particle that serves as a core, a shell layer that covers the surface of the gold nanorod particle and is formed from silver, and a copolymer that adsorbs on the surface of the shell layer, wherein the copolymer is a block copolymer or graft copolymer that is obtained by polymerizing at least a polymerizable monomer (A) that has a group represented by general formula (I):

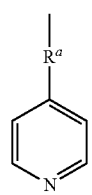

in which $R^a$ represents an alkylene group having 2-7 carbon atoms.

2. The Au—Ag core-shell nanorod particles according to claim 1, wherein the copolymer is a block copolymer or graft copolymer between the polymerizable monomer (A) and a polymerizable monomer (B) having a repeating structure represented by general formula (II):

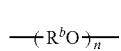

in which $R^b$ represents an alkylene group having 2-5 carbon atoms and n represents any integer from 5 to 2,000.

3. The Au—Ag core-shell nanorod particles according claim 1, wherein the polymerizable monomer (A) is represented by general formula (III):

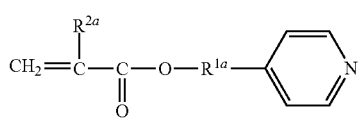

in which $R^{1a}$ represents an a kylene group having 2-7 carbon atoms and $R^{2a}$ represents a hydrogen atom or a methyl group.

4. The Au—Ag core-shell nanorod particles according to claim 2, wherein the polymerizable monomer (B) is represented by general formula (IV):

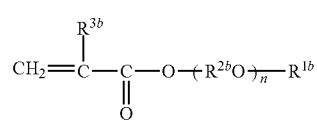

in which $R^{1b}$ is a hydrogen atom or an alkyl group having 1-10 carbon atoms, $R^{2b}$ is an alkylene group having 2-5 carbon atoms, $R^{3b}$ is a hydrogen atom or a methyl group, and n represents any integer from 5 to 2,000.

5. The Au—Ag core-shell nanorod particles according to claim 2, wherein the polymerizable monomer (B) has a weight-average molecular weight from 200 to 80,000.

6. The Au—Ag core-shell nanorod particles according to claim 2, wherein the mole ratio of the polymerizable monomer (A) to the polymerizable monomer (B) is from 1:99 to 99:1.

7. A photothermal therapy drug, comprising the Au—Ag core-shell nanorod particles according claim 1.

8. A method for producing Au—Ag core-shell nanorod particles according to claim 1, comprising:
a step of forming gold nanorod particles using a cationic surfactant as a mold,
a step of forming gold nanorod particles on which a block copolymer or graft copolymer adsorbs by substituting the cationic surfactant into the block copolymer or graft copolymer, and
a step of forming the shell layer by depositing silver on the surface of the gold nanorod particle on which the block copolymer or graft copolymer adsorbs,
wherein the copolymer is a block copolymer or graft copolymer that is obtained by polymerizing at least a polymerizable monomer (A) that has a group represented by general formula (I):

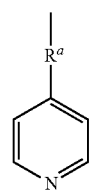

in which $R^a$ represents an alkylene group having 2-7 carbon atoms.

9. The Au—Ag core-shell nanorod particles according claim 2, wherein the polymerizable monomer (A) is represented by general formula (III):

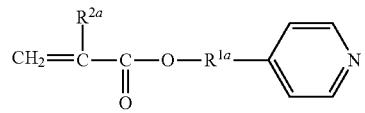

in which $R^{1a}$ represents an alkylene group having 2-7 carbon atoms and $R^{2a}$ represents a hydrogen atom or a methyl group.

10. The Au—Ag core-shell nanorod particles according to claim 4, wherein the polymerizable monomer (B) has a weight-average molecular weight from 200 to 80,000.

11. The Au—Ag core-shell nanorod particles according to claim 4, wherein the mole ratio of the polymerizable monomer (A) to the polymerizable monomer(B) is from 1:99 to 99:1.

12. The Au—Ag core-shell nanorod particles according to claim 5, wherein the mole ratio of the polymerizable monomer (A) to the polymer zable monomer (B) is from 1:99 to 99:1.

13. A photothermal therapy drug, comprising the Au—Ag core-shell nanorod particles according claim 12.

14. A photothermal therapy drug, comprising the Au—Ag core-shell nanorod particles according claim 11.

15. A photothermal therapy drug, comprising the Au—Ag core-shell nanorod particles according claim 10.

16. A photothermal therapy drug, comprising the Au—Ag core-shell nanorod particles according claim 9.

17. A photothermal therapy drug, comprising the Au—Ag core-shell nanorod particles according claim 6.

18. A photothermal therapy drug, comprising the Au—Ag core-shell nanorod particles according claim 5.

19. A photothermal therapy drug, comprising the Au—Ag core-shell nanorod particles according claim 4.

20. A photothermal therapy drug, comprising the Au—Ag core-shell nanorod particles according claim 3.

* * * * *